(12) United States Patent
Meyerhoff et al.

(10) Patent No.: US 8,697,771 B2
(45) Date of Patent: Apr. 15, 2014

(54) BIOCOMPATIBLE COATINGS, AND METHODS OF MAKING AND USING THE SAME

(75) Inventors: Mark E. Meyerhoff, Ann Arbor, MI (US); Jun Yang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 226 days.

(21) Appl. No.: 13/059,317

(22) PCT Filed: Aug. 19, 2009

(86) PCT No.: PCT/US2009/054280
§ 371 (c)(1),
(2), (4) Date: Feb. 16, 2011

(87) PCT Pub. No.: WO2010/022132
PCT Pub. Date: Feb. 25, 2010

(65) Prior Publication Data
US 2011/0144229 A1    Jun. 16, 2011

Related U.S. Application Data

(60) Provisional application No. 61/090,197, filed on Aug. 19, 2008.

(51) Int. Cl.
*A61F 2/00* (2006.01)
*A61K 9/00* (2006.01)
*A61L 33/06* (2006.01)
*C07C 391/00* (2006.01)

(52) U.S. Cl.
USPC .......... 523/112; 424/423; 424/484; 427/2.25; 562/899

(58) Field of Classification Search
USPC ................. 523/112; 424/423, 484; 427/2.25; 562/899
See application file for complete search history.

(56) References Cited

U.S. PATENT DOCUMENTS

| | | | |
|---|---|---|---|
| 7,040,756 B2 * | 5/2006 | Qiu et al. | ................. 351/159.02 |
| 2005/0008676 A1 | 1/2005 | Qiu et al. | |
| 2005/0208100 A1 | 9/2005 | Weber et al. | |
| 2006/0039950 A1 | 2/2006 | Zhou et al. | |

FOREIGN PATENT DOCUMENTS

| WO | WO 2007/005910 | 1/2007 |
|---|---|---|
| WO | WO 2007064895 A2 * | 6/2007 |

OTHER PUBLICATIONS

Preliminary Examination Report on Patentability for International Application No. PCT/US2009/054280 dated Mar. 3, 2011 (8 pages).
International Search Report for Application No. PCT/US2009/054280 dated Apr. 13, 2010 (14 pages).
Cha, W. et al., "Catalytic generation of nitric oxide from S—nitrosothiols using immobilized organoselenium species," Biomaterials, 2007, vol. 28, No. 1, pp. 19-27.

* cited by examiner

*Primary Examiner* — Michael Pepitone
(74) *Attorney, Agent, or Firm* — Dierker & Associates, P.C.

(57) ABSTRACT

Disclosed herein are biocompatible coatings for a substrate, the biocompatible coating including at least one polyanionic/polycationic bilayer including at least one nitric oxide generating moiety, wherein the polyanionic/polycationic bilayer has a layer of a polycationic polymeric material; and a layer of polyanionic material capable of non-covalently bonding to the polycationic polymeric material. Devices incorporating such coatings, and methods of making and using such coatings are also disclosed herein.

18 Claims, 23 Drawing Sheets

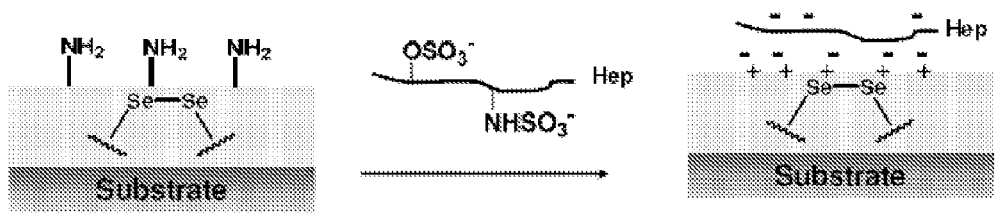
*Fig. 21 (scheme 1)*
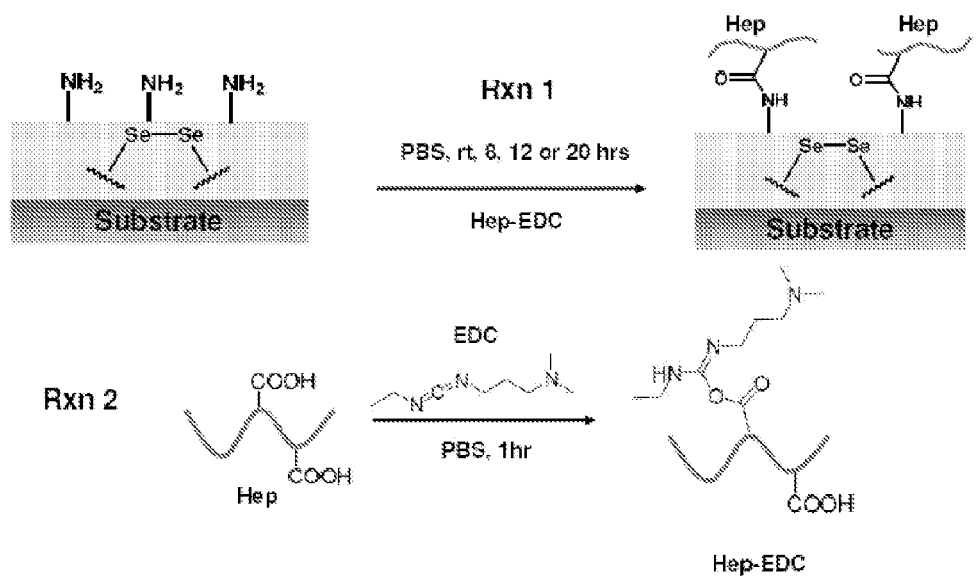
*Fig. 21 (scheme 2)*

BIOCOMPATIBLE COATINGS, AND METHODS OF MAKING AND USING THE SAME

CROSS-REFERENCE TO RELATED APPLICATIONS

This application is a U.S. National Stage Entry under 35 U.S.C. 371 of International Application Serial No. PCT/US2009/054280, filed Aug. 19, 2009, which claims priority to U.S. Provisional Patent App. Ser. No. 61/090,197, filed Aug. 19, 2008, hereby incorporated by reference in its entirety.

STATEMENT REGARDING FEDERALLY SPONSORED RESEARCH OR DEVELOPMENT

This invention was made with government support under Grant No. EB-004527 awarded by the National Institutes of Health. The government has certain rights in the invention.

RELATED APPLICATIONS

Background

Over the past several decades, cardiovascular medicine has progressed into an era where modern devices such as artificial heart valves, stents, vascular grafts, and cardiopulmonary by-pass circuits, etc. are widely employed in life-saving treatments of many patients. However, use of such devices can also promote adverse host responses, particularly risk of thrombosis. Immediately after implantation/blood contact, the surfaces of such devices adsorb plasma proteins, propagating the activation of platelets and coagulation factors, and ending in potential blood clot formation. Over the years, various surface treatments and the design of specific polymeric coatings (to reduce protein adsorption, etc.) have been explored to minimize such thrombotic risk.

Local nitric oxide (NO) release from polymeric surfaces can exert a highly effective antithrombotic effect by potently inhibiting platelet adhesion and activation. Recently, several active species have been shown capable of decomposing endogenous S-nitrosothiols (RSNO) such as S-nitrosoglutathione (GSNO), S-nitrosocysteine (CysNO), etc., to NO in the presence of free thiols as reducing agents. Further studies have revealed that these types of catalysts may be highly selective for reduction of S-nitrosothiol and/or may exhibit no catalytic activity for nitrite or nitrate reduction.

Due to its short lifetime, NO should be generated within close proximity of the surface of any implanted biomedical device to exhibit physiological activity. Confinement of the catalyst on the device surface may therefore be desirable to realize this localized and prolonged NO generation from endogenous RSNOs. Hence, proper immobilization of the catalyst plays a critical role in creating a practical surface NO generation method.

Most conventional surface modification methods involve covalently attaching molecules, including catalytic sites, on the substrate surface via a chemical reaction. However, most modern biomedical devices in use do not possess the necessary surface functionality, porosity, and geometric form to enable convenient covalent attachment of active species.

SUMMARY

The present disclosure is directed in part to a biocompatible coating for a substrate, the biocompatible coating including at least one anionic/cationic bilayer, e.g., a polyanionic/polycationic bilayer. For example, an exemplary polyanionic/polycationic bilayer may include at least one nitric oxide generating agent, e.g., an organoselenium moiety. The polyanionic/polycationic bilayer may include a layer of a cationic polymeric material, e.g., a polycationic polymeric material; and a layer of anionic material, e.g., a polyanionic material, which may be capable of non-covalently bonding to the cationic polymeric material. The nitric oxide generating agent, e.g., an organoselenium moiety, can be, in some embodiments, covalently bonded to, e.g., the polycationic polymeric material or to, e.g., the polyanionic material.

Also provided is a medical device including the biocompatible coating. In addition, disclosed herein are methods of forming a polymeric coating on a substrate capable of generating nitric oxide in-vivo, including a) providing a substrate; b) immersing the substrate into a first solution including a polycationic polymer covalently bonded to a nitric oxide generating agent, e.g., an organoselenium moiety; c) immersing the substrate into a second solution including a polyanionic polymer; and d) repeating b) and c).

BRIEF DESCRIPTION OF THE FIGURES

The embodiments and practices of the present disclosure, other embodiments, and their features and characteristics, will be apparent from the description, drawings and claims that follow.

FIG. 21 depicts two schemes for heparin surface immobilization; Scheme 1 depicts layer-by-layer immobilization; Scheme 2 depicts heparin immobilization via two different covalent attachment reactions.

DETAILED DESCRIPTION

Figure 1:
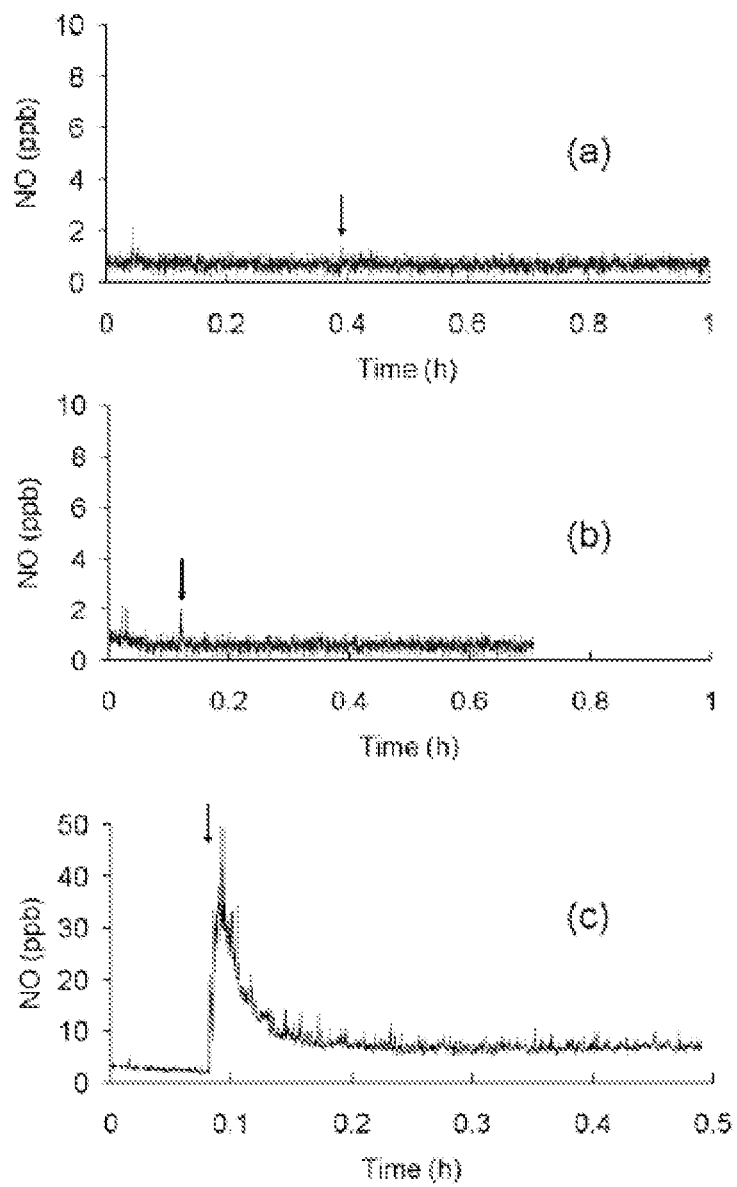
FIG. 1 includes three graphs that depict the selectivity of RSe catalyst on S-nitrosothiols, nitrite and nitrate. Five µL of 1 mg/mL SePEI solution was added into 2 mL PBS containing 0.1 mM GSH and (a) 0.1 mM $NaNO_2$; (b) 0.1 mM $NaNO_3$; and (c) 50 µM GSNO. Catalyst was added as indicated by the arrows.

This disclosure is directed, at least in part, to biocompatible coatings for a substrate that may be suitable for use with, for example, medical devices.

The biocompatible coating may include at least one anionic/cationic bilayer, e.g., a polyanionic/polycationic bilayer, including at least one nitric oxide generator (e.g., an organoselenium moiety or a plurality of organoselenium moieties). Each polyanionic/polycationic bilayer includes a layer of a polycationic polymeric material and a layer of polyanionic material capable of non-covalently bonding to the polycationic polymeric material. Furthermore, in one example, the nitric oxide generator (e.g., an organoselenium moiety) is covalently bonded to the polycationic polymeric material or to the polyanionic material.

In one embodiment, the polycationic polymeric material includes at least one of: polyethyleneimine, chitosan, or quaternized polyamide. For example, the polycationic polymeric material may include polyethyleneimine (PEI).

In one embodiment, the polyanionic polymeric material includes at least one of sodium alginate, cellulose sulfate, heparin, hyaluronic acid, or polyglutamic acid. In another embodiment, the polyanionic polymeric material is sodium alginate (Alg).

The organoselenium moiety may be selected, for example, from the group consisting of: selenocystamine, selenocystine, 3,3'-diselenodipropionic acid, selenocysteine, ebselen, propyl-selenocystine, allyl-selenocystine, methyl-selenocystine, selenomethionine, selenium choline, or a diselenium compound. In one non-limiting example, the organoselenium moiety is 3,3'-diselenodipropionic acid.

In one embodiment, the at least one organoselenium moiety may be covalently bonded to the polycationic polymeric material, or the at least one organoselenium moiety may be covalently bonded to the polyanionic polymeric material. In some embodiments, at least one organoselenium moiety is covalently bonded to the polyanionic polymeric material and to the polycationic material.

Exemplary structures of i) PEI (i.e., an example of the polycationic polymeric material) covalently bound to a diselenide (SePEI) (i.e., an example of the organoselenium moiety) and ii) Alg (i.e., an example of the polyanionic polymeric material) include:

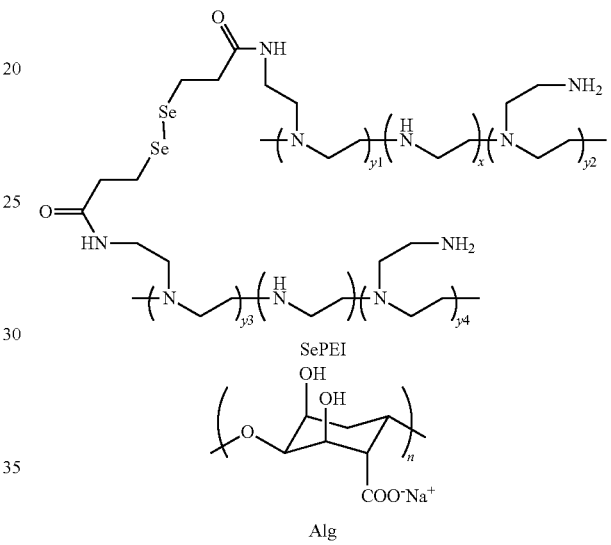

In one embodiment, the biocompatible coating includes at least four polyanionic/polycationic bilayers. However, it is to be understood that the biocompatible coating may include at least about five, at least about ten, at least about fifteen, or any other desirable number of the polyanionic/polycationic bilayers. For example, the coating may include from about 9 bilayers to about 20 bilayers, or from about 2 bilayers to about 300 bilayers, or any range therebetween (e.g., from about 50 bilayers to about 200 bilayers). For example, such biocompatible coatings may include (SePEI/Alg)$_n$, where n ranges from about 2 to about 300, and may be any number or range therebetween (e.g., n may be 5, 10, 15, 20, or in a range of about 10 to about 200).

In an embodiment, the coating may include SePEI as an "outer" layer which then may be associated (e.g., covalently bond to, directly or indirectly) with another active moiety, such as heparin. In another embodiment, the biocompatible coating includes from about 1 μg/cm$^2$ to about 4 μg/cm$^2$ Se when the coating is placed on the substrate.

Non-limiting examples of suitable substrates include at least one of a polymer, ceramic, or a metal (e.g., a biologically acceptable metal). In one embodiment, the substrate includes polyurethane or silicone.

Also provided herein is a medical device that is at least partially coated with the biocompatible coating disclosed herein. Non-limiting examples of such medical devices include an intravascular or extravascular medical device, a balloon, a catheter tip, a prosthetic heart valve, a suture, a surgical staple, a synthetic vessel graft, a stent, a stent graft, a vascular or non-vascular graft, a shunt, an aneurysm filler, an intraluminal paving system, a guide wire, an embolic agent, a filter, a drug pump, an arteriovenous shunt, an artificial heart valve, an artificial implant, a foreign body introduced surgically into the blood vessels or at a vascular or non-vascular site, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor, an interventional cardiology device, a catheter, and plastic tubing.

Also provided herein, and discussed further hereinbelow, are methods of forming a polymeric coating on a substrate capable of generating nitric oxide in-vivo, including a) providing the substrate; b) immersing the substrate into a first solution including a polycationic polymer covalently bonded to an organoselenium moiety; c) immersing the substrate into a second solution including a polyanionic polymer; and d) repeating b) and c).

In one embodiment, the method further includes immersing the substrate in an annealing solution including glutathione or S-nitrosoglutathione; and phosphate buffered saline. It is to be understood that the substrate is immersed in the annealing solution for at least about one day, for example from about 1 day to about 4 days.

Without being limited to any theory, it is believed organoselenium compounds, when exposed to endogenous or exogenous sources of nitrates, nitrites, or nitrosothiols (optionally in the presence of reducing agents), generate nitric oxide (NO) and/or an active species that generates NO within and/or at the surface of the selected substrate. For example, an organoselenium moiety, e.g., RSe or those others disclosed herein, can be covalently bound to a polycationic polymer that can be coated on the substrate using layer by layer technology, where the polycationic polymer is established such that it is alternating with a polyanionic polymer. Such a coating can include one or more bilayer formed on, e.g., the previously mentioned substrate, and may possess immobilized RSe (or another suitable organoselenium) moieties. Contacting such a biocompatible coating with a source of RSNOs, e.g., blood or another bodily fluid may form NO by catalytically decomposing these endogenous NO carriers.

In one embodiment, a diselenide moiety such as 3,3'-diselenidediproprionic acid is covalently bound to PEI (polyethyleneimine), as shown in the SePEI structure above, wherein x, $y_1$, $y_2$, $y_3$, and $y_4$ can each vary from 1 to 1000.

In one embodiment, the polycationic polymer may be labeled with a chromophore, such as fluorescein-5-isothiocyanate, to aid in detection by UV-Vis spectroscopy.

Substrates for coating may be first optionally coated with another polymer, e.g., a cationic polymer that does not contain selenium, such as for example, polydiallyldimethylammonium chloride. Such coating may be followed by another polymer, e.g. Alg to form a precursor layer onto which subsequent layers are built or assembled. For example, the substrate may be immersed in a first solution including the polycationic polymer covalently bonded to the organoselenium moiety, such as SePEI. Then, the substrate can be immersed into a second solution including the polyanionic polymer, such as Alg. This process is repeated for as many bilayers as are desired.

Figure 3:
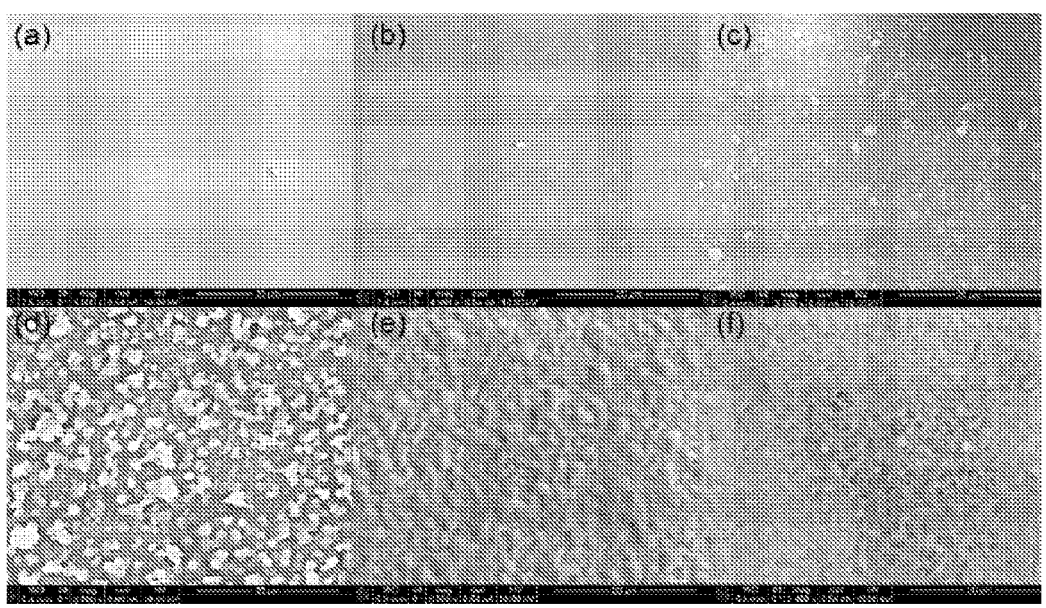
FIGS. 3a-3f depict scanning electron micrographs (SEMs) of $(SePEI/Alg)_n$ layers on a quartz slide for n=0-5.

The resulting bilayer and/or coating may have increasing UV-Vis absorbance of the labeled selenide polycationic polymer as the number of layers increases. For example, analysis by scanning electron micrography indicates that while the initial bilayers may form small particles on the surface of the substrate, continuous deposition significantly smoothes the surface and leads to more modest surface irregularities (see FIG. 3).

In some embodiments, a layer-by-layer adsorption may result in a heterogeneous film structure which may be thermodynamically unstable. An annealing process may reduce the existing defects through self-rearrangement of polymer chains. For example, in some embodiments, annealing in the presence of, e.g., glutathione (GSH) may provide a film with greater clarity, as compared to a film or coating without such annealing. Without being limited by any theory, the presence of GSH likely facilitates the healing process by reducing most of the diselenide crosslinks and yielding SePEI polymers that are smaller in size and that more readily rearrange into a more thermodynamically stable conformation. Annealing may also lead to a film or coating with greater stability in retaining its Se content.

Embodiments of the biocompatible coatings disclosed herein may also be characterized by their static contact angles. For example, if a pre-coating with a cationic polymer that does not contain selenium is used, bilayers initially exhibit similar contact angles regardless of which polyionic species is the outermost layer. As more bilayers are formed, the back-and-forth change of surface tension further verifies the bilayer buildup of the film by alternate deposition of polycationic and polyanionic polymers.

Figure 9:
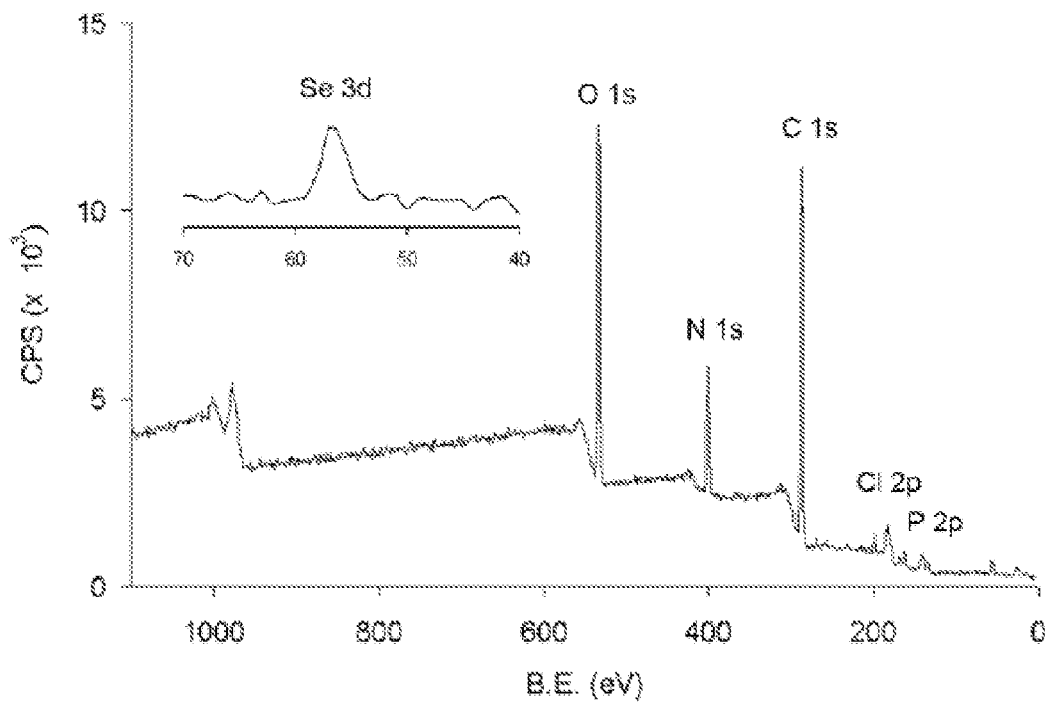
FIG. 9 depicts the X-ray photoelectron spectroscopy of $(SePEI/Alg)_{15}$ on a quartz substrate.

The chemical composition of the bilayers can be studied using X-ray photoelectron spectroscopy, which can confirm the presence of immobilized Se in the film (see FIG. 9). In one example, SePEI was shown to have about a quarter of the nitrogen atoms in a quaternized state. This results from the high degree of secondary and tertiary amines in the polymer. Taking into account this partial ionization, SePEI polymers have been shown to have ratios of cation:anion at about 1:1. This ratio indicates that very few small counterions are embedded in the bilayer.

Figure 7:
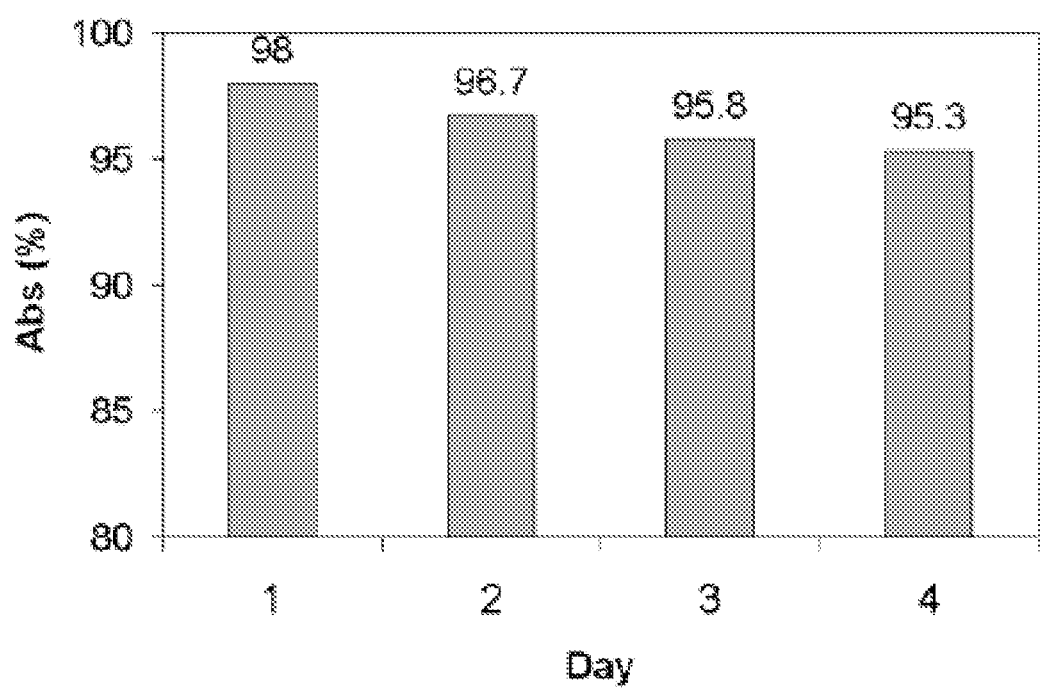
FIG. 7 depicts UV-Vis stability studies on $(SePEI/Alg)_5$ coated on the inner wall of a quartz cuvette.

The catalytic activity of the biocompatible coating can be determined, for example, from monitoring NO generation from S-nitrosoglutathione (GSNO) with glutathione as a reducing agent. A chemiluminesence assay can be performed using a commercially available NO analyzer (NOA), such as one from Sievers 280 (Boulder, Colo.). The results shown in FIG. 7 illustrate the increase in NO production when the coating contacts the GSNO/GSH solution and the drop in production when the coating is removed from the solution. In one embodiment, the NO concentration may flux from about 0 ppb to about 60 ppb, or at any range therebetween, such as from about 5 ppb to about 50 ppb, or from about 8 ppb to about 40 ppb. The NO flux degrades slightly over time which is likely attributed to the consumption of the GSNO in the bulk test solution. Although GSNO can directly react with GSH to produce nitroxyl and potentially compete with the catalytic GSNO decomposition, the reaction rate for nitroxyl formation is much slower and the RSe catalyst dependent GSNO decomposition is the primary reaction by which GSNO is consumed in the reaction mixture. The marginal baseline increase after coated substrate removal may suggest that only a very small amount of catalyst leaches from the bilayer film into the test solution, with no severe delamination of the catalytic multilayer observed. Indeed, the return to baseline in the chemiluminescence experiments after removing the coated substrate may be a very sensitive means to probe the degree of leaching, since any loss of RSe species will induce a homogenous reaction which is much faster than the heterogeneous surface reaction mediated by the LbL (layer-by-layer) process.

In some embodiments, bilayer assembly that had not been annealed shows significant NO generation from bulk solution, indicating substantial catalyst leaching from the LbL assembly into the test solution. For example, FIG. 13 indicates enhanced stability of the LbL assembly that is induced by the annealing step. Studies also show that thicker films do not block access of GSNO to the inner layers of the coating (see FIG. 12). The degree of NO generation from given RSNO/RSH concentrations can be controlled by the number of bilayers deposited. The biocompatible coatings disclosed herein may also possess significant catalytic activity over time. In one non-limiting example, continuous NO production occurs for at least 24 hours, and in another non-limiting example, continuous NO production occurs for at least 48 hours.

The biocompatible coating disclosed herein may produce NO when introduced to biological fluids, such as blood. Without spiking additional GSNO, the endogenous GSNO and other RSNO concentrations in the blood decrease rapidly due to the consumption by the catalyst. The concentration of endogenous S-nitrosothiols found in human blood includes S-nitrosoalbumin, 0.25-7 µM; S-nitrosoglutathione, 0.02-0.2 µM; S-nitrosocysteine, 0.2-0.3 µM; and S-nitrosohemaglobin, 0.3-0.003 µM. In one embodiment, the NO concentration generated by a disclosed coating is about, for example, 100 ppb to about 150 ppb when the coating at least partially coats the substrate, and the substrate is placed in contact with blood. These coatings can preserve significant activity after exposure to blood components for an extended time period.

In an exemplary embodiment, disclosed biocompatible coatings may be deposited on silicone rubber and polyurethane catheters. For example, the silicone rubber surface may be charged by silanization with 3-aminopropylsilane (APS), adsorption of PDDA, and adsorption of SePEI. Alternatively, the biocompatible coatings disclosed herein may be used, for example, on or in a medical device, and in some embodiments, on a metal surface of a medical device. "Medical device", as used herein, refers to any intravascular or extravascular medical devices, medical instruments, foreign bodies (including implants), and the like. Examples of intravascular medical devices and instruments include balloons or catheter tips adapted for insertion, prosthetic heart valves, sutures, surgical staples, synthetic vessel grafts, stents (e.g., Palmaz-Schatz, Wiktor, Crown, Mutlilink, GFX stents), stent grafts, vascular or non-vascular grafts, shunts, aneurysm fillers (including GDC, Guglilmi detachable coils), intraluminal paving systems, guide wires, embolic agents (for example, polymeric particles, spheres and liquid embolics), filters (for example, vena cava filters), drug pumps, arteriovenous shunts, artificial heart valves, artificial implants, foreign bodies introduced surgically into the blood vessels or at vascular or non-vascular sites, leads, pacemakers, implantable pulse generators, implantable cardiac defibrillators, cardioverter defibrillators, defibrillators, spinal stimulators, brain stimulators, sacral nerve stimulators, chemical sensors, breast implants, interventional cardiology devices, catheters, and the like. Examples of extravascular medical devices and instruments include plastic tubing, dialysis bags or membranes whose surfaces come in contact with the blood stream of a patient. Contemplated metals that may be coated using the disclosed coatings may be biomedically acceptable for in-vivo use, as are known in the art. Such metals may include stainless steel, Co—Cr alloys, titanium, titanium alloys, nitinol (a nickel titanium alloy), and metallic biomaterials having magnesium and/or iron.

After a device or artificial material has been coated at least partially with an embodiment of the biocompatible coating as disclosed herein, it will be substantially suitable for its intended use, including, for example, implantation as a heart valve, insertion as a catheter, insertion as a stent, or for cardiopulmonary oxygenation or hemodialysis.

Also disclosed herein are methods for the administration of a therapeutically effective amount of NO generated by the biocompatible coatings described herein for treating cardiovascular diseases and disorders including, for example, restenosis, vasospasm, atherosclerosis, and diseases where vasodilation of arteries is indicated. A therapeutically effective amount may be, for example, based on the amount of a biocompatible coating necessary to provide a therapeutically effective amount of nitric oxide.

The term "therapeutic effect" is art-recognized and refers to a local or systemic effect in animals (particularly mammals, and more particularly humans) caused by a pharmacologically active substance. The term thus means any substance intended for use in the diagnosis, cure, mitigation, treatment or prevention of disease, or in the enhancement of desirable physical or mental development and/or conditions in an animal or human. The phrase "therapeutically-effective amount" means that amount of such a substance produces some desired local or systemic effect, or for example, generates an amount of nitric oxide to produce some desired effect, at a reasonable benefit/risk ratio applicable to any treatment. The therapeutically effective amount of such a substance will vary depending upon the subject and disease condition being treated, the weight and age of the subject, the severity of the disease condition, the manner of administration, and the like, all of which can readily be determined by one of ordinary skill in the art. For example, certain compositions of the coatings disclosed herein may be administered in a sufficient amount to produce a reasonable benefit/risk ratio applicable to such treatment.

Another embodiment of the disclosure provides methods for the inhibition of platelet aggregation and platelet adhesion caused by the exposure of blood (including blood components or blood products) to a medical device. Such methods include depositing a biocompatible coating on the medical device and disposing said medical device on or in a patient.

A method is also provided to promote healing and/or endothelialization of intravascular luminal surfaces in a patient in need thereof, for example, to promote endothelialization of unstable/ulcerated atherosclerotic plaque, for example in coronary/carotid arteries, or on de-endothelialized luminal surfaces such as those found following an endarterectomy, for example within the carotid artery, a thrombectomy (either/or arterial/venous), an angioplasty, such as balloon, laser, or cryogenic angioplasty, an atherectomy, or following thrombolysis, by administering a composition disclosed herein.

The biocompatible coatings provided herein may also assist in resolution of acute, or chronic arterial and/or venous thrombosis, for example revascularization and/or neovascularization and/or recanalization.

The compositions disclosed herein may also improve biocompatibility of, e.g., an implantable device such as a sensor, as compared to an implantable device that does not include a biocompatible coating of the present disclosure. For example, a device including a biocompatible coating as disclosed herein may be placed in the body, for example, for twice the duration as compared to a device without the disclosed composition, with substantially little or no adverse effect to the patient.

In treating cardiovascular diseases and disorders, the biocompatible coating disclosed herein may be administered directly to the damaged vascular or non-vascular surface intravenously by using an intraarterial or intravenous catheter that is suitable for delivery of the compositions to the desired location. For example, the disclosed coatings, disposed on a medical device, may be used generate nitric oxide in-vivo. The location of damaged arterial surfaces is determined by conventional diagnostic methods, such as X-ray angiography, performed using routine and well-known methods available to one skilled in the art.

"Cardiovascular disease or disorder" refers to any cardiovascular disease or disorder known in the art, including, but not limited to, restenosis, coronary artery disease, atherosclerosis, atherogenesis, cerebrovascular disease, angina, ischemic disease, congestive heart failure or pulmonary edema associated with acute myocardial infarction, thrombosis, high or elevated blood pressure in hypertension, vasospasm, platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neoinitimal hyperplasia following percutaneous transluminal coronary angiograph, and the like. Complications associated with the use of medical devices may occur as a result of increased platelet deposition or activation, thrombus formation, consumption of platelets, and coagulation of proteins. Such complications, which are within the definition of "cardiovascular disease or disorder," include, for example, myocardial infarction, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury resulting from, such as, for example, angioplasty, balloon dilation, atherectomy, laser ablation treatment or stent insertion. Restenosis may also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery.

"Blood" includes blood products, blood components and the like.

The disclosure having been generally described, it will be more readily understood by reference to the following examples which are included merely for purposes of illustration of certain aspects and embodiments of the present disclosure, and are not intended to limit the disclosure in any way.

EXAMPLES

Materials

Polyethyleneimine (PEI, Mw 25 kD), polydiallyldimethylammonium chloride (PDDA, Mw 100-200 kD), sodium alginate (Alg, Mw 12-80 kD) (FIG. 1(b)), glutathione (GSH), fluorescein-5-isothiocyanate (FITC), sodium borohydride (NaBH$_4$), 1-(3-diethylaminopropyl)-3-ethylcarbodiimide (EDC), N-hydroxysuccinimide (NHS), 2-(N-Morpholino) ethanesulfonic acid (MES), and 2-(N-cyclohexylamino)-ethanesulfonic acid (CHES) were obtained from Sigma-Aldrich (St. Louis, Mo.). The 3140 RTV Silicone Rubber was purchased from Dow Corning Corporation (Midland, Mich.). All reagents were used as received except for alginate, a solution of which was first membrane filtered (Durapore® 0.1 µM, Millipore Corp. (Billerica, Mass.)) to remove insoluble impurities before use. 3,3'-Diselenidedipropionic acid (SeDPA) and S-nitrosoglutathione (GSNO) were synthesized as described previously. All solutions were prepared with 18 MΩcm$^{-1}$ deionized distilled water obtained from a Milli-Q system (Millipore Corp., Billerica, Mass.).

Example 1

Preparation of Organoselenium Immobilized Polyelectrolyte (SePEI)

SePEI (FIG. 1(a)) was synthesized following a procedure slightly modified from the one reported earlier. (Cha, W.; Meyerhoff, M. E. Biomaterials 2007, 28, (1), 19-27.) SeDPA (76 mg, 0.25 mmol) was activated with EDC (285 mg, 1.5 mmol) and NHS (115 mg, 1 mmol) and the reaction mixture was allowed to react with PEI (20 mg) in MES buffer (pH=6.0) for 2 h. The resulting SePEI was separated by centrifuging the mixture in an Amicon® centrifugal filter unit (MWCO=3 kD, Millipore Corp., Billerica, Mass.) at 4,000 rpm for 40 min. The SePEI was initially reduced with NaBH$_4$ to break any diselenide crosslinks into selenols, and then was exhaustively dialyzed (Spectra/Por® 7, MWCO=3.5 kD, Spectrum Laboratories Inc., Rancho Dominguez, Calif.) in 50 mM NaCl for 3 days to remove any unreacted —SeC$_2$H$_4$COOH halves. The dialyzed solution was then further concentrated into a yellow viscous solution and stored at 4° C. until use. The yellow color indicated the reformation of diselenide bonds between PEI chains due to oxidation of selenols by ambient O$_2$ during dialysis. Nevertheless, the crosslinked SePEI still exhibited good solubility in water as suggested by the absence of any precipitation.

Lyophilized SePEI samples were weighed and digested using 1 mL 100% fuming nitric acid at room temperature. The digesting solutions were brought to 10 mL using volumetric flasks and quantified using ICP-MS. The Se content in the SePEI polymer was determined to be 6.6±0.1 wt (0.85±0.01 mmole g$^{-1}$) of dry polymer as shown in Table 1.

TABLE 1

Percent Se in SePEI as determined by ICP-MS

|   | $W_{total}$ (mg) | $C_{Se}$ (ug/mL) | w/w % |
|---|---|---|---|
| 1 | 6.6 | 42.6 | 6.5 |
| 2 | 8.3 | 55.4 | 6.7 |
| 3 | 4.0 | 26.7 | 6.7 |

$W_{total}$: Mass of lyophilized SePEI polymer samples.
$C_{Se}$: Concentration of Se in digesting solution determined by ICP-MS.
w/w %: gravimetric percentage of Se in the lyophilized polymer.

To determine the selectivity of the RSe catalyst on S-nitrosothiols, nitrite and nitrate, five µL of 1 mg/mL SePEI solution was added into 2 mL PBS containing 0.1 mM GSH and (a) 0.1 mM NaNO$_2$; (b) 0.1 mM NaNO$_3$; (c) 50 µM GSNO. As shown in FIG. 1, catalyst was added as indicated by the arrows. The results show that the organoselenium based catalyst can efficiently decompose S-nitrosothiols in the presence of free thiols as reducing agent; however, the catalyst displays no activity on nitrite or nitrate reduction.

Example 2

Labeling of SePEI with FITC Chromophore

The SePEI polymer was labeled with FITC chromophore ($\epsilon_{495}$=76,000 $M^{-1}$ $cm^{-1}$) to render the polymer spectroscopically visible. SePEI in CHES (2 mg $mL^{-1}$, 10 mL) was mixed with FITC/DMF solution (1 mg $mL^{-1}$, 0.8 mL) under constant stirring for 1 h. The resulting orange adduct was washed, concentrated and re-dissolved in PBS for subsequent use. The labeling degree was calculated to be 0.53 using protocol provided by Sigma Aldrich. (http://www.sigmaaldrich.com/sigma/product%20information%20sheet/f4274pis.pdf.) This labeled SePEI was exclusively employed for all UV-Vis studies to observe stepwise deposition of SePEI during the LbL process.

Example 3

Construction of NO Generating LbL Films on Quartz Surfaces

All polyelectrolytes were prepared as 1 mg $mL^{-1}$ solutions: PDDA was dissolved in CHES (pH=9.3), while SePEI and Alg were made in PBS (pH=7.4). The quartz substrate (either slide or cuvette) was cleaned in piranha solution (3:7 v/v $H_2SO_4/H_2O_2$ mixture) for 30 min before use to fully remove surface impurities. The LbL multilayer was then prepared by immersing the substrate alternately into the polycation (SePEI or PDDA) and polyanion (Alg) solutions for 10 min with washing with PBS buffer after each deposition step. A (PDDA/Alg)$_2$ film was coated as a precursor layer to stabilize and amplify the surface charge on the substrate. Then, SePEI and Alg were deposited alternately until a desired number of (SePEI/Alg) bilayers were formed. A reductive annealing process followed the step-by-step deposition to further stabilize the polyelectrolyte structure. The freshly prepared LbL was immersed in a 20 mL disposable scintillation vial filled with 100 μM GSH in PBS. The vial was wrapped with aluminum foil and kept at room temperature overnight before the catalytic activity of the resulting LbL was examined.

Figure 2:
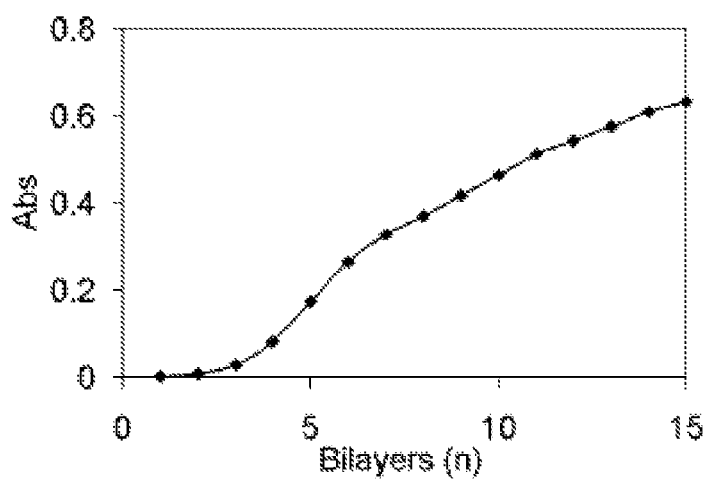
FIG. 2 is a graph depicting the absorbance at 503 nm of $(SePEI/Alg)_n$ after the assembly of each bilayer.

Due to FITC tracer, the (SePEI/Alg)$_n$ displays a maximum absorbance at 503 nm which was extracted and plotted against the number of bilayers in the LbL. As shown in FIG. 2, the absorbance displays an ascending trend suggesting that the quantity of SePEI on the substrate increases continuously during the LbL deposition.

Example 4

Characterization of (SePEI/Alg)$_n$ on Quartz Substrate by UV-Vis Spectroscopy The stepwise growth of the LbL film was monitored using a UV-Vis spectrophotometer (Lambda 35, Perkin Elmer, Mass.). The LbL was constructed on the inner wall of a quartz cuvette by filling the cuvette with polyelectrolyte solutions in the sequence described in Example 3 above. The cuvette was then scanned from 550 nm to 450 nm with a data interval of 1 nm after every (SePEI/Alg) bilayer was deposited. The FITC labeled SePEI species was employed exclusively in these studies.

Example 5

Characterization of (SePEI/Alg)$_n$ on Quartz Substrate by XPS

X-ray photoelectron spectroscopy was performed on a Kratos Axis Ultra XPS (Kratos Analytical, England). The X-ray source employed was a monochromatized Mg Kα operated at 10 kV/80 W with pass energy of 80 eV. Charge neutralization was used to compensate the charge accumulation on the sample. The coating was scanned at step sizes of 1 eV and 0.1 eV (0.1 s each step) for survey and core scans, respectively. Prior to the measurement, the sample was outgassed overnight in the sample transfer chamber under high vacuum. The spectrum was processed using CasaXPS version 2.3.12.

Figure 10:
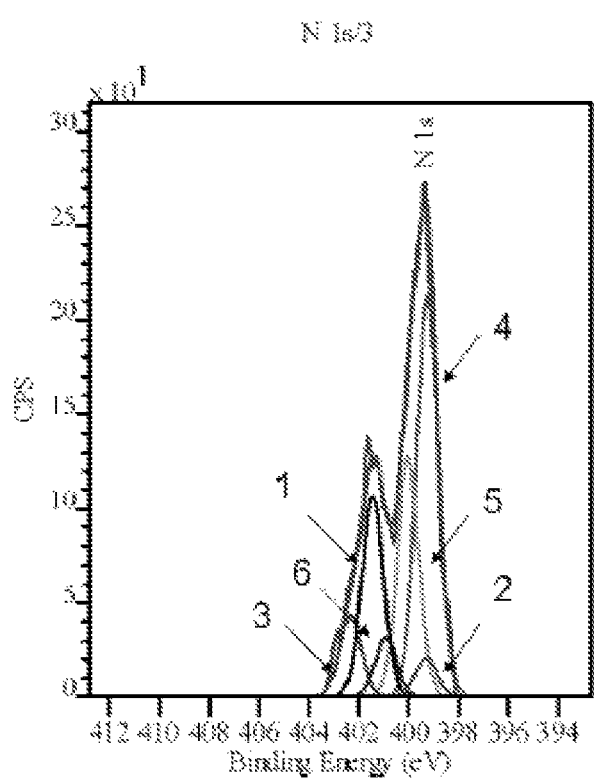
FIG. 10 depicts curve fitting of N1s envelope in XPS core scan.

As shown in FIG. 9, the spectrum peak at 57 eV was identified as Se 3d electron, which confirms the immobilization of organoselenium species within the multilayer. Slight amounts of Cl and P were also found in the film, probably from the $H_2PO_4^-$ and $Cl^-$ small ions in the buffer in which the LbL was deposited. The amine:carboxylate ratio was determined to be 3.89 based on the atomic percentage of N and O. FIG. 10 depicts fitting of N1s envelope in XPS core scan, which shows that only 27.5% of the SePEI amines are in their ionized cationic form. Such a low ionization degree is expected for branched PEI in which a great amount of secondary and tertiary amines distribute densely on the polymer backbone.

Example 6

Characterization of (SePEI/Alg)$_n$ on Quartz Substrate by SEM

Surface morphology of the polyelectrolyte multilayers was examined on a FEI Nova Nanolab Scanning Electron Microscope via the detection of secondary electrons. The specimens were dried in a $N_2$ atmosphere overnight and then gold coated using a SPI Sputter Coater at 18 mA for 60 seconds for better imaging.

FIGS. 3a-3f depict scanning electron micrographs (SEMs) of (SePEI/Alg)$_n$ layers on a quartz slide for n=0-5. The initial (PDDA/Alg)$_2$ precursor layer provided a smooth and even coverage on the quartz substrate (FIG. 3a). One (SePEI/Alg) bilayer only slightly roughened the surface with scattered islands that are hardly distinguishable from the background owing to their small dimensions (FIG. 3b). When more layers of the polyelectrolytes were deposited, the tiny islands quickly developed into coalesced large particles with a maximum diameter of about 2 μm, which considerably roughen the surface (FIGS. 3c-d). The PEI crosslinked by the diselenides possesses a bulkier conformation compared with linear polyelectrolytes, and this further sterically impedes the effective interaction of the SePEI with the substrate. As a result, little adsorption of SePEI results in accumulation of enough positive charge to reverse the surface potential, which explains the slow increase in UV-Vis adsorption (see FIG. 2) for the first couple of coating steps.

A full coverage of the surface is finally realized after 4 bilayers (FIG. 3e); however, the earlier coarse structure can still be vaguely recognized from the bumpy surface contour. Continuous deposition of polyelectrolytes significantly smoothes the bumpiness and leads to more modest surface irregularities (FIG. 3f). The transition from discrete particles to continuous layer as well as the subsequent smoother surface can be attributed to the propensity of polyelectrolytes to bridge over the underlying defects.

Figure 4:
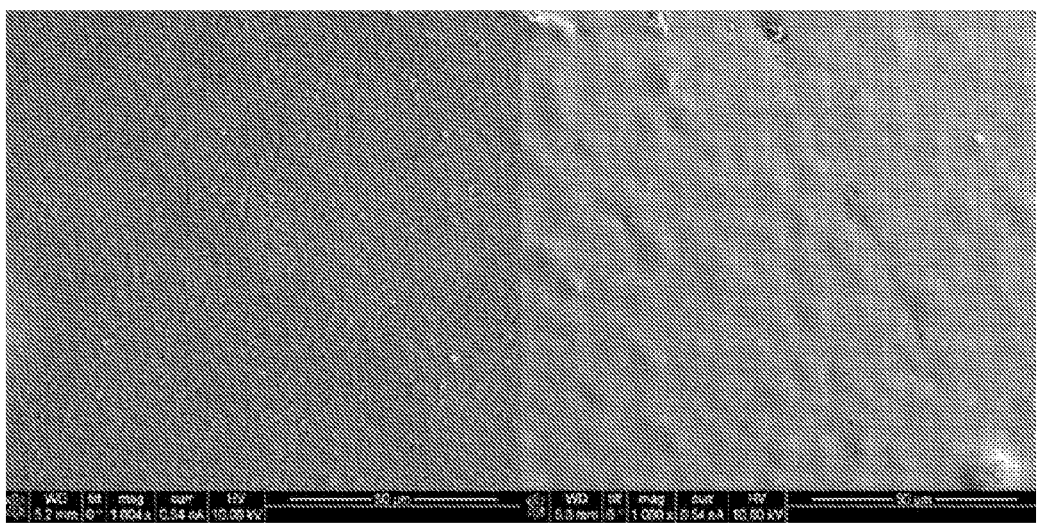
FIG. 4 depicts SEMs of $(SePEI/Alg)_5$ coated on a quartz slide before (left) and after (right) annealing in PBS containing 100 µM GSH.

An annealing process as described in Example 3 is therefore desirable (and in many instances may be required) to reduce the existing defects through self-rearrangement of polymer chains. FIG. 4 depicts SEM of (SePEI/Alg)$_5$ coated on a quartz slide before (left) and after (right) annealing in PBS containing 100 μM GSH. The fuzzy appearance of freshly coated LbL surface develops into a denser layer embedded with coarse clumps up to 10 μm in diameter after annealing. Such a surface conformational change further verifies the occurrence of chain rearrangement.

Figure 5:
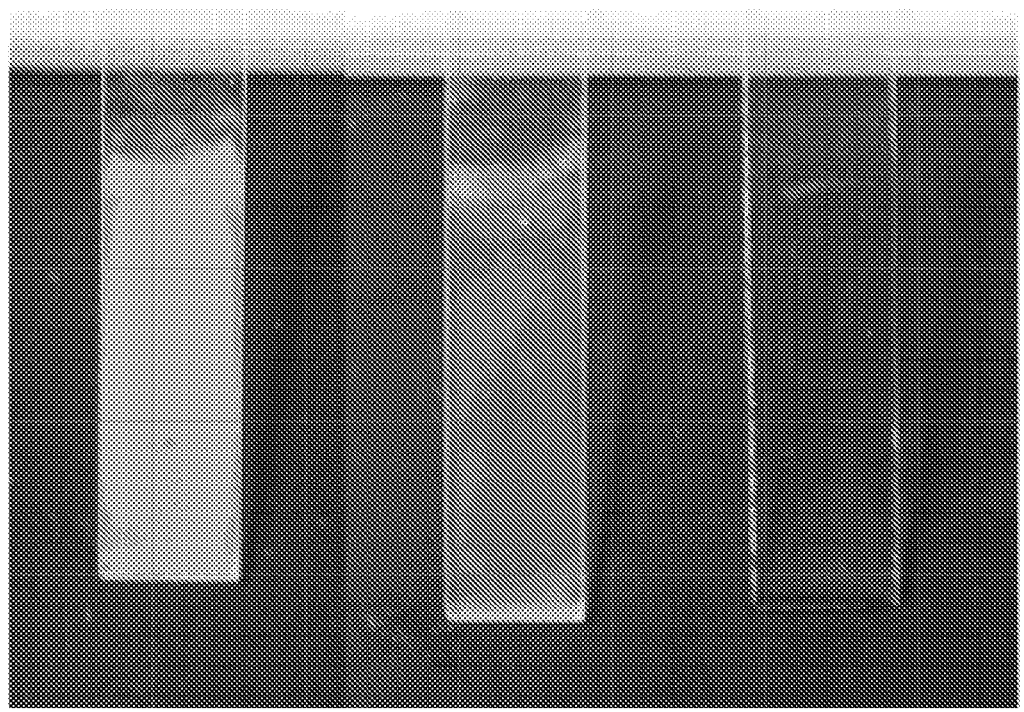
FIG. 5 depicts the annealing effect on the appearance of $(SePEI/Alg)_5$ the sample on the left was a freshly assembled LbL film on a quartz slide which exhibits a cloudy appearance; the sample in the middle was the LbL annealed in PBS without GSH; and the sample on the right was the LbL after having been annealed in PBS containing GSH.
Figure 6:
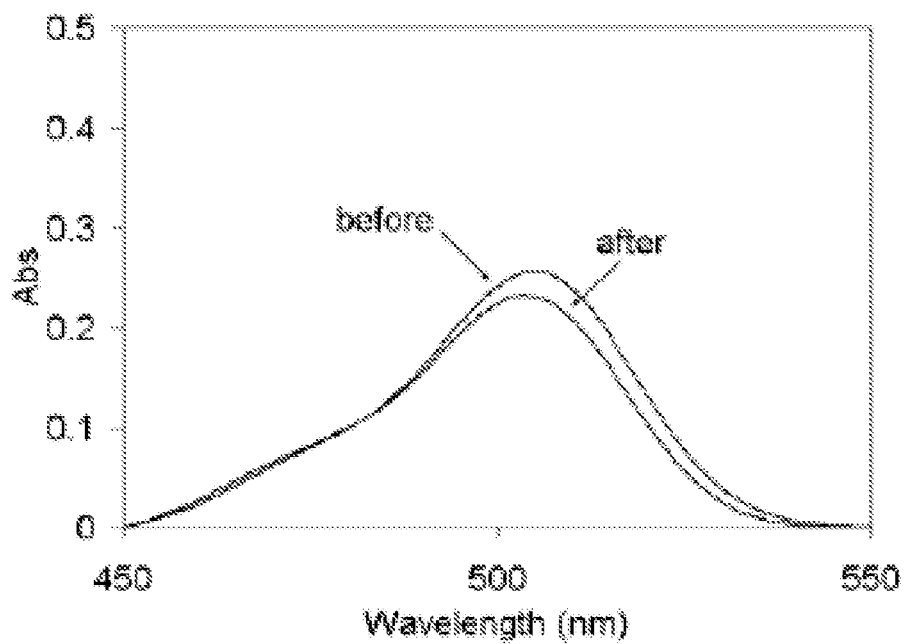
FIG. 6 depicts a UV-Vis spectra of $(SePEI/Alg)_5$ before and after annealing.

FIG. 5 depicts the annealing effect on the appearance of (SePEI/Alg)$_5$ where the annealed bilayer has greater clarity. FIG. 6 depicts a UV-Vis spectra of (SePEI/Alg)$_5$ before and after annealing, showing that the annealed LbL retains 92.2% of its clarity. FIG. 7 depicts UV-Vis stability studies on a (SePEI/Alg)$_5$ coated on the inner wall of quartz cuvette. After 4 days exposure in PBS in presence of 100 μM GSH and 50 μM GSNO, the multilayer preserves 95.3% of its original UV-Vis adsorption.

Example 7

Characterization of (SePEI/Alg)n on Quartz Substrate by Contact Angle

Static air-water contact angles were measured by a sessile drop method using a Cam-100 Optical Contact Angle Goniometer (KSV Instruments Ltd., Monroe, Conn.) at ambient humidity and temperature. The annealed LbL coated on glass slides were dried with N$_2$ flow for 2 days. For each polymer surface, 4 drops were examined to obtain the average contact angle values.

Figure 8:
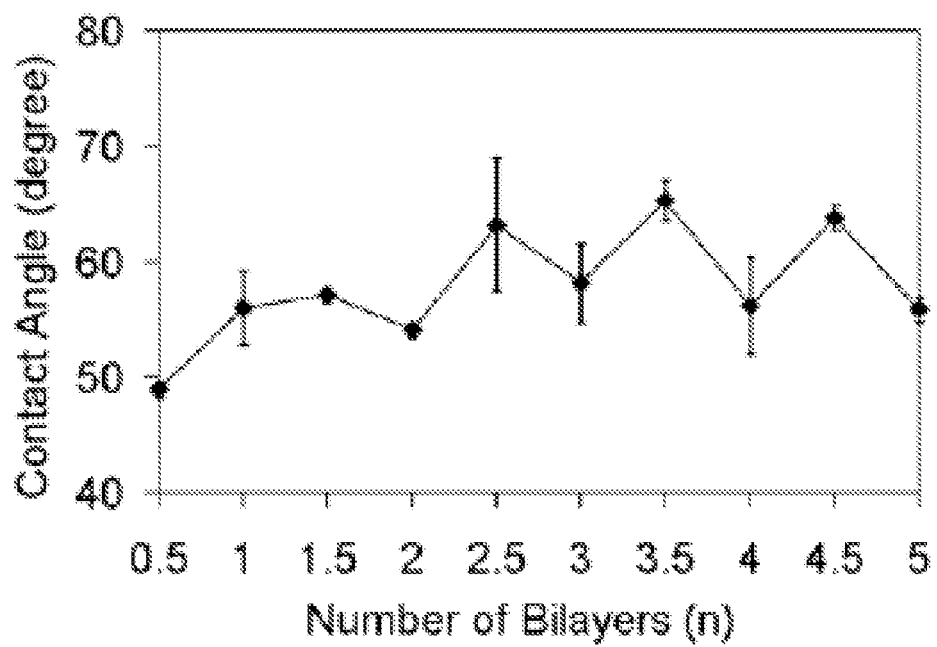
FIG. 8 is a graph depicting the contact angles from $(SePEI/Alg)_n$ films having a different number of absorbed layers of polyelectrolytes. Integral numbers represent films with Alg as the outermost layer, otherwise SePEI is the outermost layer.

FIG. 8 depicts the contact angles from (SePEI/Alg)$_n$ films having a different number of absorbed layers of polyelectrolytes. Integral numbers represent films with Mg as the outermost layer, otherwise SePEI is the outermost layer. From the 3$^{rd}$ coating cycle onward, the contact angles fluctuate periodically between 64.1±3.3 for the SePEI as the outermost layer and 56.7±3.1 for Alg as the outermost layer. This back-and-forth change of surface tension further verifies the LbL buildup of the film by alternate deposition of SePEI and Alg.

Example 8

Characterization of (SePEI/Alg)n on Quartz Substrate: NO Detection

The catalytic activity of (SePEI/Alg)$_n$ deposited on a quartz slide was investigated by measuring NO generation from GSNO with GSH as the reducing agent via chemiluminescence. Slides coated with (SePEI/Alg)$_n$ LbL films were inserted into a PBS (2 mL, pH=7.4) test solution containing GSNO and GSH. The coating area that was submerged by the test solution and therefore involved in the catalytic reaction was about 3 cm$^2$. The NO produced was purged from the solution with N$_2$ flow and detected using a chemiluminescence NO analyzer (NOA) (Seivers 280, Boulder, Colo.). The amount of NO evolved from the solution was calculated based on the calibration curves of the NOA, which were obtained regularly by plotting the integrated NOA signal (ppb s) during calibration vs. the introduced amount (moles) of NO into the system via nitrite reduction in an acidified potassium iodide solution. To prevent unwanted RSNO decomposition from external thermal or photo stimuli, all NOA tests were performed at room temperature using amber reaction vessels and low light conditions. EDTA was added to the testing solution in order to eliminate any GSNO decomposition catalyzed by trace metal ions, e.g., Cu(II).

Figure 11:
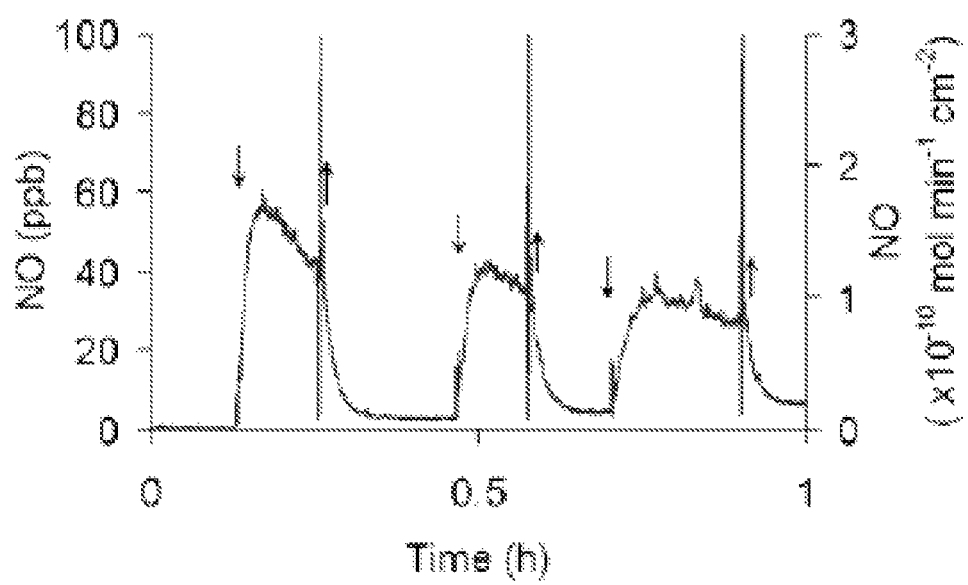
FIG. 11 depicts an NO analysis (NOA) of $(SePEI/Alg)_5$ coated on a quartz slide in PBS containing 50 µM GSNO, 50 µM GSH and 0.1 mM EDTA. The slide was immersed (↓)/removed (↑) as indicated by the arrows.

FIG. 11 depicts an NOA of (SePEI/Alg)$_5$ coated on a quartz slide in PBS containing 50 μM GSNO, 50 μM GSH and 0.1 mM EDTA. The slide was immersed (j)/removed (0 as indicated by the arrows in the Figure. Nitric oxide production is initiated instantly upon introducing the slide into the test solution and plateaus at a sustained NO level rapidly. When the slide is removed, the NO generation ceases almost entirely, indicating that the catalytic GSNO breakdown occurs predominantly in the LbL film on the slide. Repeated immersion and removal of the slide replicate the up-and-down NO generation pattern. The NO flux degrades slightly over time, which is likely attributed to the consumption of the GSNO in the bulk test solution. The marginal baseline increase after slide removal suggests only a very small amount of catalyst leaches from the LbL film into the test solution during the measurements, with no severe delamination of the catalytic multilayer being observed.

Figure 12:
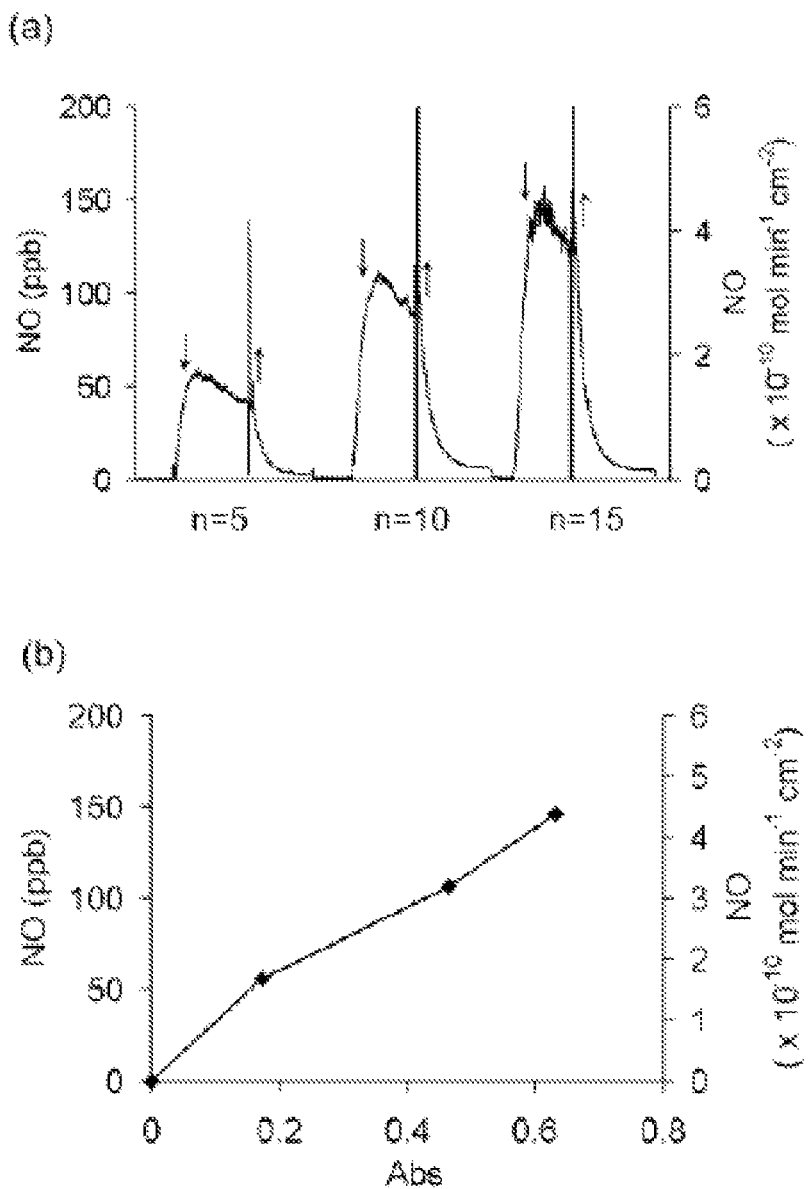
FIG. 12a is a graph depicting the maximum NO flux($\times 10^{-10}$ mol min$^{-1}$ cm$^{-2}$) and NO concentration (ppb) as a function of the number of bilayers in the (SePEI/Alg)$_n$.
FIG. 12b is a graph depicting the NO flux and concentration vs. absorbance at 503 nm.

FIG. 12 depicts the maximum NO flux and NO concentration as a function of the number of bilayers in the (SePEI/Alg)$_n$. FIG. 12b depicts the NO flux and NO concentration vs. absorbance at 503 nm. These results show an increase in observed NO production for thicker films. The maximum NO flux increases as NO concentration increases from 56 ppb for (SePEI/Alg)$_5$ to 106 and 146 ppb for (SePEI/Alg)$_{10}$ and (SePEI/Alg)$_{15}$, respectively. The background solution phase NO generation (after slide removal) does not show a significant increase for the greater number of bilayers deposited. This suggests that the enhanced NO production is derived from the access to the RSe catalyst in the underlying layers of the LbL coating.

Figure 13:
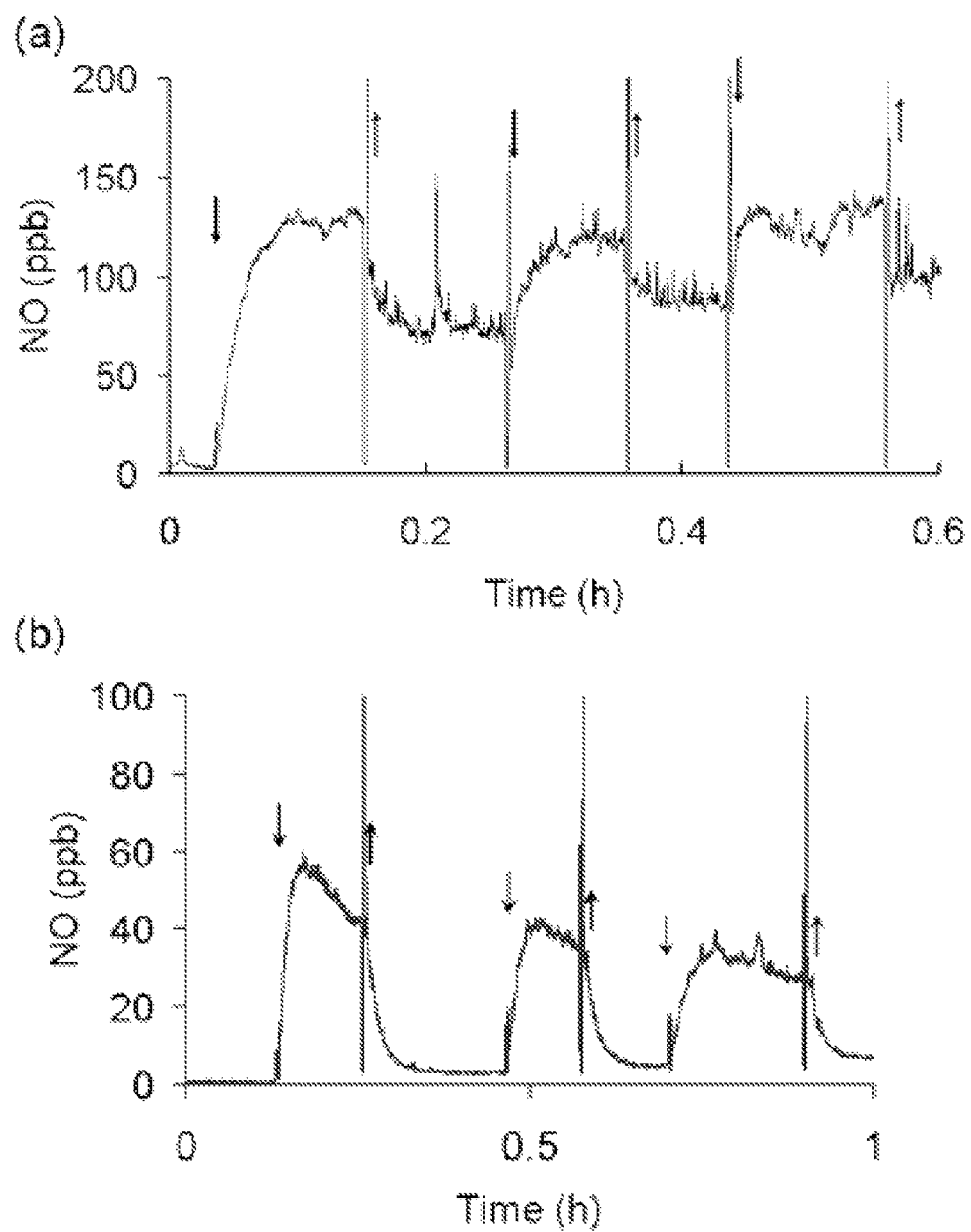
FIG. 13 depicts NOA studies of (a) fresh prepared (unannealed) and (b) annealed (SePEI/Alg)$_5$ in PBS containing 50 μM GSNO and 50 μM GSH.

FIG. 13 depicts NOA studies of (a) fresh prepared (unannealed) and (b) annealed (SePEI/Alg)$_5$ in PBS containing 50 μM GSNO and 50 μM GSH. A significant NO generation from bulk solution in a) was observed, indicating substantial catalyst leaching from the un-annealed LbL into the test solution.

Figure 14:
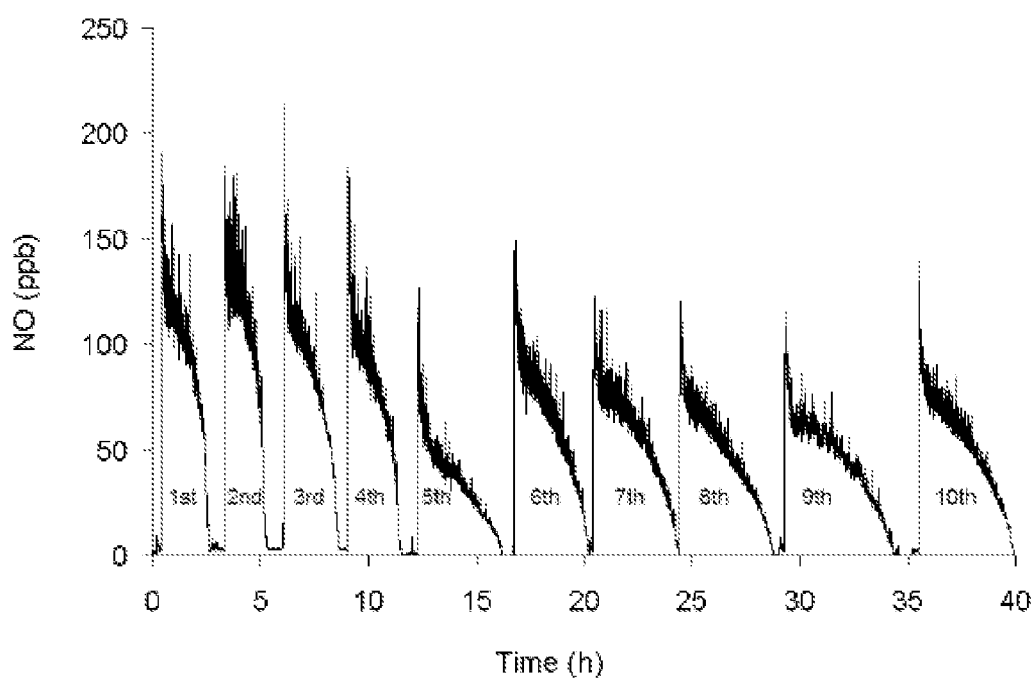
FIG. 14 is a graph depicting long term NO generation on a slide coated with (SePEI/Alg)$_{10}$. 10 batches of PBS (2 mL each) containing 50 μM GSNO and 100 μM GSH were allowed to react with the catalytic LbL successively.

FIG. 14 depicts long term NO generation on a slide coated with (SePEI/Alg)$_{10}$. 10 batches of PBS (2 mL each) containing 50 μM GSNO and 100 μM GSH were allowed to react with the catalytic LbL successively. The LbL was kept in each test solution until the NO production fully stopped and subsequently transferred to the next test solution. After continuously reacting for 40 h in total, the LbL still exhibited significant catalytic activity. The conversion rate of GSNO was calculated separately for all 10 reactions revealing that the GSNO in each batch was completely depleted. The estimated Se content in the LbL was 0.11 μmol, while the total GSNO decomposed was 1 μmol. The extended reaction time also resulted in a slower kinetics. Compared with the 1$^{st}$ batch, the maximum NO flux in the 10$^{th}$ experiment decreases about 60%, while the time required to decompose all the GSNO is almost doubled.

Example 9

Characterization of (SePEI/Alg)n on Quartz Substrate: In Vitro Blood Test

Fresh heparinized (5 U mL$^{-1}$) sheep whole blood was obtained from ECMO Laboratory in the Medical School at the University of Michigan. 3 mL of blood was carefully transferred into a 15 mL polypropylene centrifuge tube. A glass slide coated with (SePEI/Alg)$_{10}$ was gently positioned in the blood. The tube was sealed and wrapped with aluminum foil to reduce light exposure. During the entire procedure, the blood surface was kept below the top of the coating to avoid any accidental contact with bare glass. After 24 h incubation at 4° C. in the dark, the slide was removed and rinsed with PBS buffer to wash off any loosely adsorbed blood residue. A control slide was immersed in 3 ml PBS and processed following the same procedure. The ability of the resulting LbL to generate NO from GSNO was then examined by the chemiluminescence method described Example 8 above.

Figure 15:
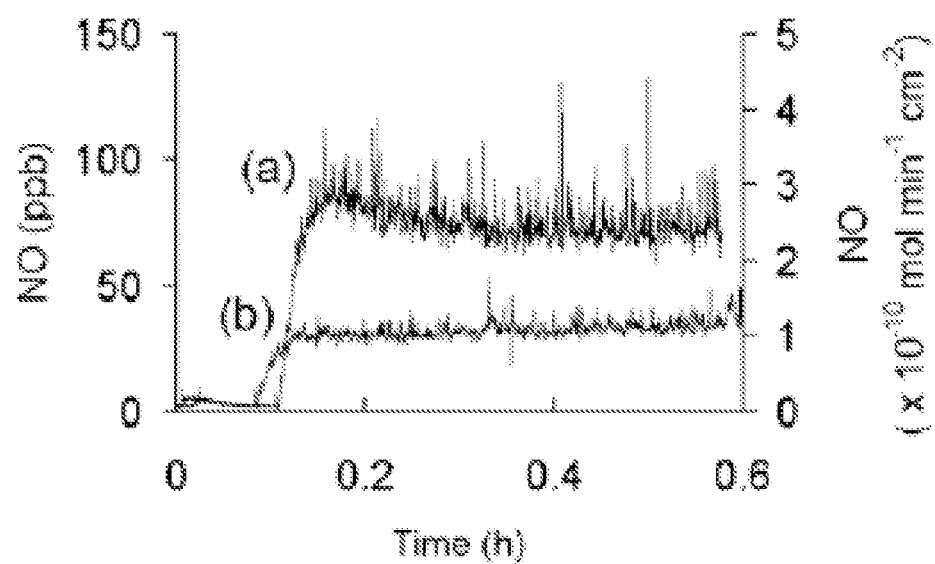
FIG. 15 depicts an NO analysis of (SePEI/Alg)$_{10}$ after 24 h incubation in (a) PBS; and (b) sheep whole blood.

FIG. 15 depicts an NOA of $(SePEI/Alg)_{10}$ after 24 h incubation in (a) PBS; (b) sheep whole blood. The endogenous GSNO and other RSNO concentrations in the blood decrease rapidly due to the consumption by the catalyst. After 24 h of contact, the LbL in sheep's blood was thus partially covered by thrombus (since NO generation ceases without more substrate). When the blood clots were carefully peeled off with tweezers, the LbL underneath still displayed significant catalytic activity in generating NO from a fresh GSNO/GSH solution (FIG. 15b) and was able to fully convert all the GSNO added in the reaction. However, the LbL in contact with blood displayed a lower NO generating activity (about 50% less) compared with the control (FIG. 15a) which had been in contact only with PBS buffer.

Example 10

Quantification of Se in $(SePEI/Alg)_{10}$

A slide (1×2 cm) coated with 10 (SePEI/Alg) bilayers was placed in a vial containing 4 ml, 100% fuming nitric acid. The polyelectrolyte film immediately peeled off from the slide upon acidification and floated freely in the acid. The vial was capped and kept at room temperature for 24 h during which the LbL broke down into a number of small pieces. Then, the acid was brought to 60° C. until all these small pieces were completely digested. The digesting solution was brought to a volume of 25 mL using a volumetric flask and the Se content was measured using ICP-MS. Another vial containing same amount of nitric acid but without the multilayer was also prepared following the same protocol and was used as a control.

Example 11

Se Leaching Test $(SePEI/Alg)_{10}$ was coated on glass shell vials (1.5 cm ID, 3.5 cm, Fischerbrand®, Fischer Scientific Inc., Pittsburgh, Pa.). The coating area was calculated to be 12.4 cm². Four mL of PBS buffer containing 100 μM GSH and 50 μM GSNO was added to each vial, which is enough to submerge the entire coating area, to extract leachable selenium species from the LbLs. The vials were then capped, wrapped with aluminum foil, and kept at room temperature for 5 days. Every 24 hours, the extracting solutions were collected and the vials were refilled with fresh PBS buffer containing the same concentration of GSH and GSNO. After a 5 day extraction period, the LbLs were digested using nitric acid as described in Example 10 above to quantify the remaining Se in the coatings. The extracts and digesting solutions were brought up to a volume of 25 mL for subsequent ICP-MS measurements.

The following results, shown in Table 2, were obtained, and indicate the minimal amount of Se leaching from the $(SePEI/Alg)_{10}$ bilayer.

TABLE 2

Selenium quantification and leaching test of $(SePEI/Alg)_{10}$ as measured by ICP-MS

| | $C_L$ (μg/mL) | $C_T$ (μg/mL) | % | C (μg/cm²) |
|---|---|---|---|---|
| 1 | 0.5 | 1.41 | 3.4 | 2.9 |
| 2 | 0.4 | 1.40 | 2.8 | 2.9 |
| 3 | 0.4 | 1.41 | 2.8 | 2.9 |

$C_L$: Se concentration in extracting solution.
$C_T$: Se concentration in digesting solution.
%: percent Se leached out from the LbL during the 5 d extraction period.
C: Se content per unit area in $(SePEI/Alg)_{10}$.
(1) % is calculated using:
$$\% = 100 * \frac{C_L}{C_L + C_T}$$
(2) C is calculated following:
$$C = \frac{\text{total Se}}{\text{film area}} = \frac{(C_L + C_T) * 25 \text{ ml}}{12.4 \text{ cm}^2}$$

Example 12

Preparation of Polymeric Substrates for LbL Deposition

Silicone tubing (0.64 mm ID/1.19 mm OD, 2 cm), purchased from Helix Medical Inc. (Carpinteria, Calif.), and 5 Fr double lumen polyurethane catheter (Cook, Denmark) were cut into 1 inch segments. The open ends of these segments were sealed with RTV 3140 SR followed by curing under ambient conditions overnight. Before immersion in polyelectrolyte solutions for LbL deposition, the polymeric substrates were cleaned by sonicating in deionized $H_2O$ and ethanol for 20 min each. The silicone rubber was soaked in PBS overnight before placing into a PDDA solution, whereas the polyurethane substrate was directly coated with $(SePEI/Alg)_n$ without a precursor layer.

Figure 16:
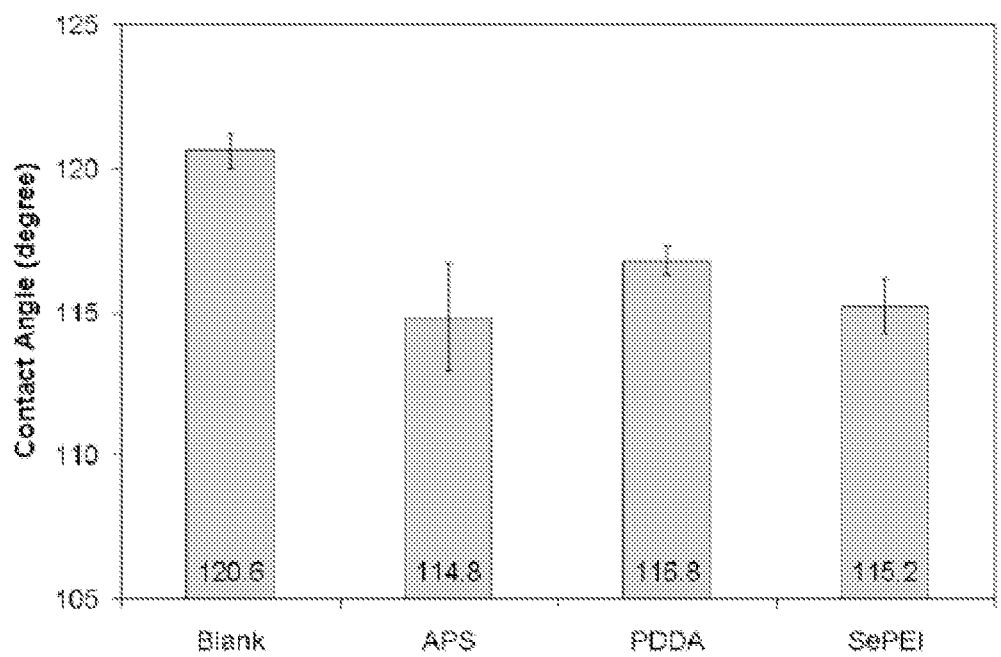
FIG. 16 is a graph depicting comparative contact angle measurements on silicone rubber surfaces adsorbed with 3-aminopropylsilane (APS), PDDA, and SePEI.
Figure 17:
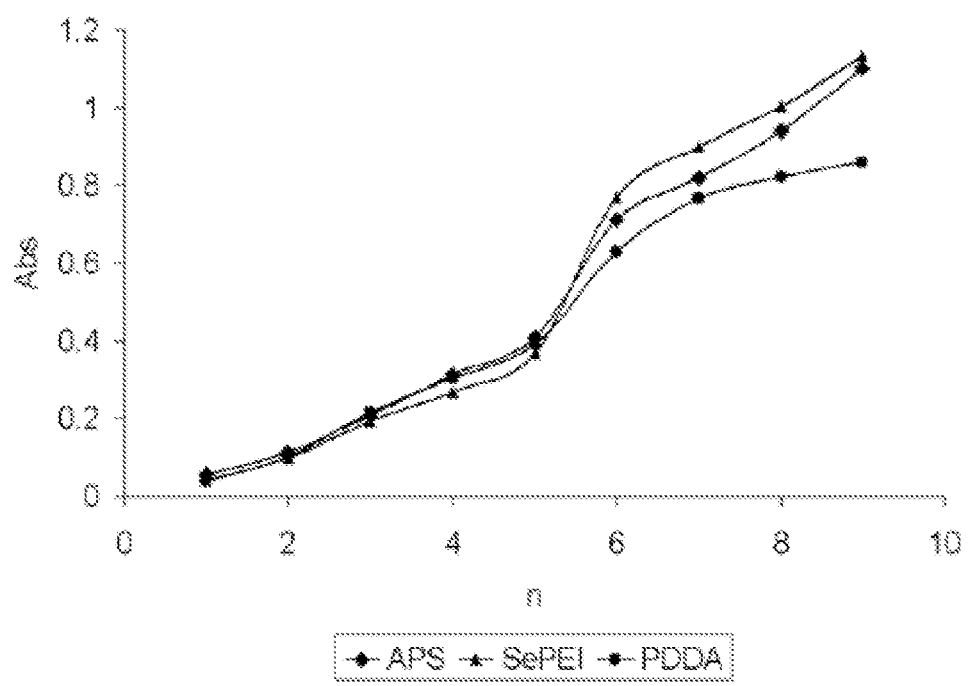
FIG. 17 depicts UV-Vis studies of (SePEI/Alg)$_n$ buildup on silicone rubber treated with different charged polymers: silanization with 3-aminopropylsilane (APS), adsorption of PDDA, and adsorption of SePEI.

FIG. 16 depicts contact angle measurements on silicone rubber surfaces adsorbed with different polymer. Glass slides were dip-coated with RTV Silicone Rubber (20% in THF) and cured in ambient condition overnight before utilized as flat silicone substrates. The silicone substrates were then immersed in solutions containing 3-aminopropylsilane (APS), PDDA, and SePEI for 2 hours. Another slide was immersed in PBS for the same amount of time and used as a blank. The contact angles were measured using the same method described in Example 7. All three methods lower the surface contact angle of the silicone rubber by 4-6°. The surface charge of the treated (charged) silicone tubing was reversed by a layer of Alg and further stabilized with $(PDDA/Alg)_2$ before $(SePEI/Alg)_n$ LbL film was assembled. UV-Vis studies reveal little disparity in the stepwise growth of the resulting LbLs, regardless of the various surface charging methods employed (FIG. 17).

Figure 18:
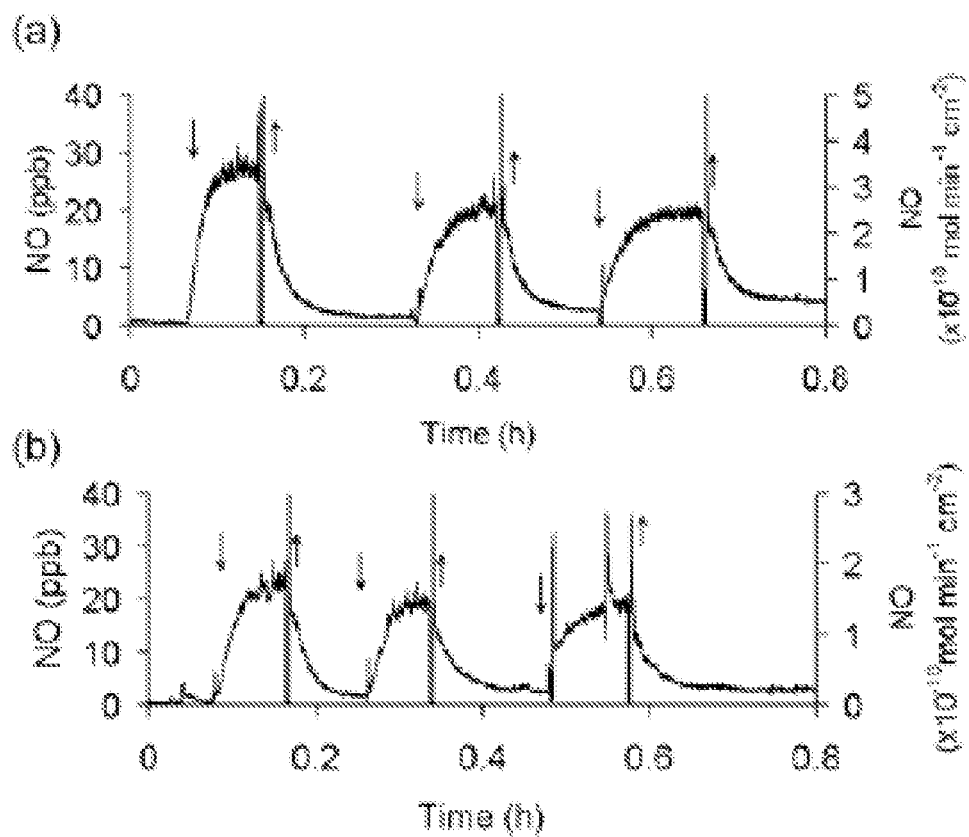
FIG. 18 depicts NO Analysis of (SePEI/Alg)$_{10}$ on a) silicone rubber tubing and on b) polyurethane (PU) catheter. The segment of polyurethane catheter or silicone rubber tubing was immersed (↓)/removed (↑) as indicated by the arrows.

FIG. 18a depicts NOA of $(SePEI/Alg)_{10}$ on a) silicone rubber tubing and on b) PU catheter. The results show the NO generation from $(SePEI/Alg)_{10}$ on silicone tubing upon repeated immersion and removal of the LbL coated tubing into a solution of 50 μM GSNO and 50 μM GSH in PBS buffer. The catalytic behavior of the film on silicone rubber is quite similar to that observed on quartz. FIG. 18b shows the NO generation from $(SePEI/Alg)_{10}$ assembled on the surface of PU-based catheters without a precoating with $(PDDA/Alg)_2$ precursor layers. The normalized NO fluxes observed when in contact with a 50 μM GSNO and 50 μM GSH solution are $2.4 \times 10^{-10}$ and $1.8 \times 10^{-10}$ mol min⁻¹ cm⁻² for silicone and PU substrates, respectively.

Example 13

Animal Toxicity Test (SePEI/Alg)$_n$ LbL (layer by layer) was tested for systemic toxicity and irritation response using animal models following ISO standards 10993-11 and 10993-10, respectively. (SePEI/Alg)$_{20}$ coatings with area of 28.96 cm$^2$ were coated on glass vials and extracted with 12 ml phosphate saline or vegetable oil at 37° C. under constant agitation for 72 hours.

Figure 19:
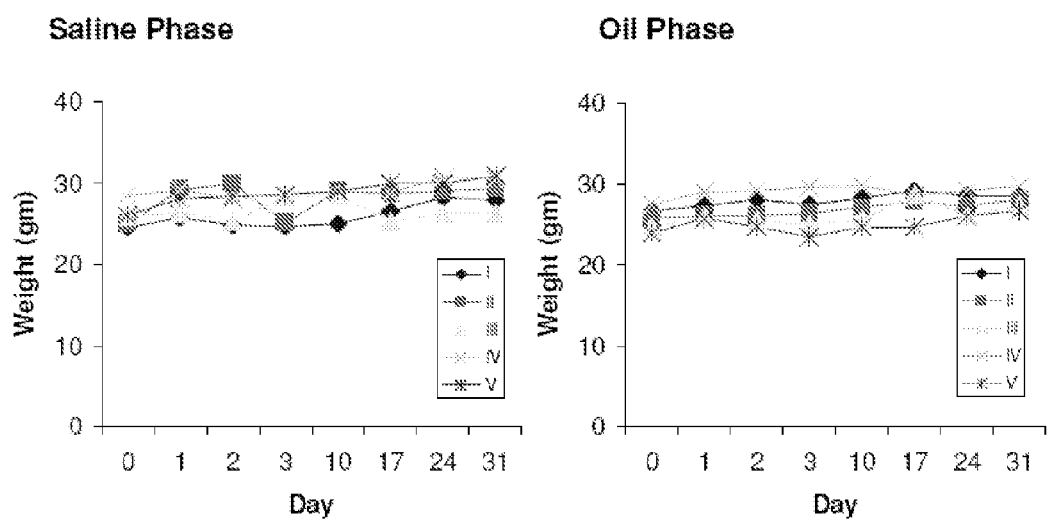
FIG. 19 depicts the results of a systemic toxicity test (in saline and oil) of (SePEI/Alg)$_{20}$ in mice.

For the system toxicity test, ISO 10993-11 protocol was used. Two groups of 5 mice were administrated with 0.1 ml saline phase extract intravenously for one group and 0.15 ml oil phase extract intraperitoneally for the other. Results are shown in FIG. 19 (control group not shown). After 28 days of observation, neither group developed obvious weight loss, which indicates any leachables, existing in the extracts, do not have potential systemic toxicity.

For the irritation test, ISO 10993-10 protocol was used. 0.2 ml oil phase extract was injected intradermally to rabbit, no irritation responses were observed.

Example 14

Commercial Fabrication

Figure 20A:
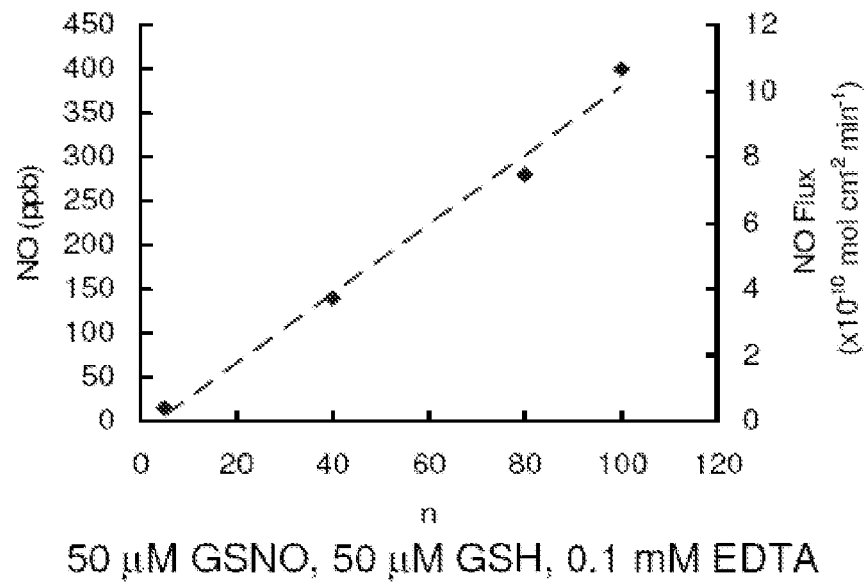
FIG. 20A depicts the permeability of LbL to GSH and GSNO reactants.

The LbL film/assembly can be fabricated using a commercial automated coating instrument, e.g. StratoSequence series manufactured by Nanostrata (nanostrata.com). The NO generation from these machine coated LbLs show positive correlation to the number of bilayers for up to 100 bilayers, indicating the multilayer possesses certain permeability that allows substantially all the RSe sites within the film to participate in the reaction. FIG. 20A shows that GSH and GSNO reactants can diffuse through the entire coating, (here, deposited on quartz) even when the number of layers is 100.

Figure 20B:
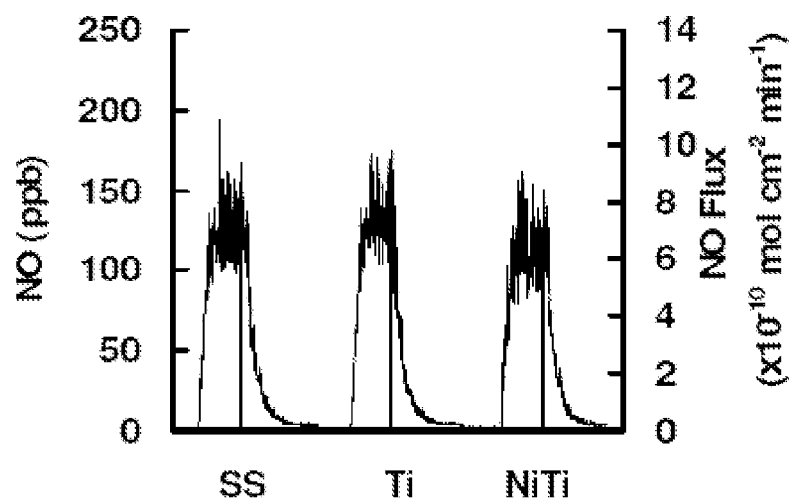
FIG. 20B depicts NO generation from a coating on stainless steel, titanium, and nitinol.

(SePEI/Alg)$_n$ coating was fabricated on stainless steel, titanium, and nitinol without any priming of the metal surfaces except for a brief rinsing to remove any dust residues. A NO generation experiment was conducted using NO generation from 50 mM GSNO, 50 mM GSH by (SePEI/Alg)$_{150}$ coated on biomedical grade stainless steel (SS), titanium (Ti), and nitinol (NiTi). Results shown in FIG. 20B indicates that the LbL can be easily adapted onto commercial available biomedical surfaces without significantly change their catalytic activity.

Figure 20C:
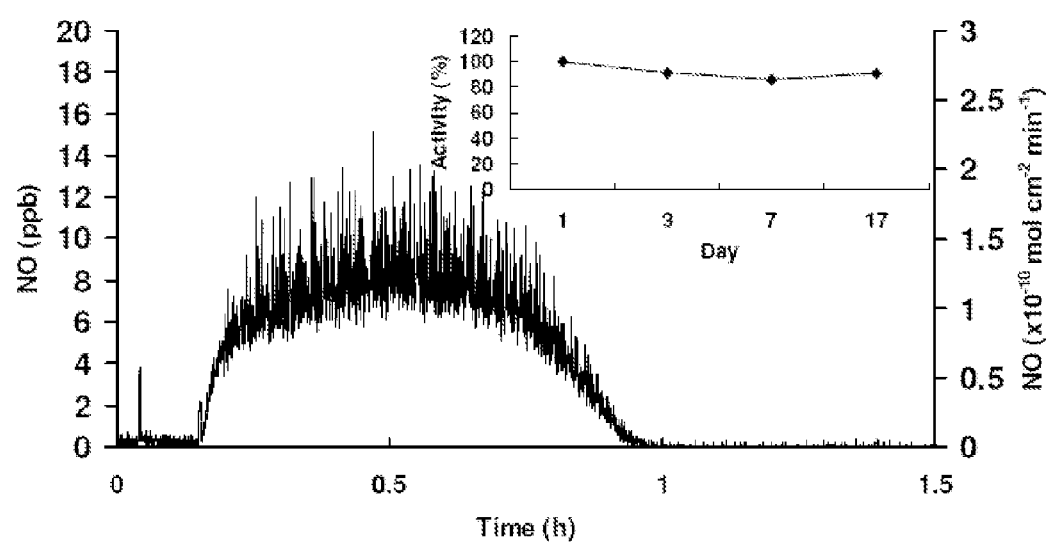
FIG. 20C depicts NO generation from biological levels of RSNO and RSH.

Automatically coated (SePEI/Alg)$_{100}$ is able to generate a NO flux of $1.5 \times 10^{-10}$ mol cm$^{-2}$ min$^{-1}$ from physiological concentrations of GSNO and GSH, as shown in FIG. 20C. This NO flux is comparable to the basal NO flux produced by human endothelium. The coating displays marginal activity decrease over prolonged soaking in PBS. Activity (shown in FIG. 20C insert) has been followed for up to 17 days after fabrication, but a much longer life time is within reasonable estimation.

Example 15

Heparin Immobilization—LbL Deposition

Coatings can also be prepared with SePEI as the outermost layer, i.e., (SePEI/Alg)$_{100}$SePEI, if the deposition is terminated after adsorption a cationic SePEI layer. In this circumstance, the amine sites on the surface can be used to immobilized other anticoagulants (such as heparin) to bring about a synergic function with NO. The heparin molecule, which is also an anionic polysaccharide, can be immobilized using a similar LbL process on (SePEI/Alg)$_n$SePEI with SePEI as counter polyion, as presented in Scheme 1 of FIG. 21.

Example 16

Heparin Surface Immobilization-Covalent Attachment

Heparin can be covalently attached to the amine carrying surface via an amide bond, as depicted in Rxn 1, Scheme 2 of FIG. 21. To promote the immobilization, the carboxylate groups on heparin may be pre-activated using N-(3-Dimethylaminopropyl)-N'-ethylcarbodiimide hydrochloride (EDC), as depicted in Scheme 2, Rxn 2 of FIG. 21. Then, the (SePEI/Alg)$_n$SePEI surface is immersed in a buffer containing 1 mg/ml activated heparin (using a PBS buffer) and allowed to react for a given amount of time, i.e., 8, 12 or 20 hours.

Example 17

Activity of Immobilized Heparin

Figure 22:
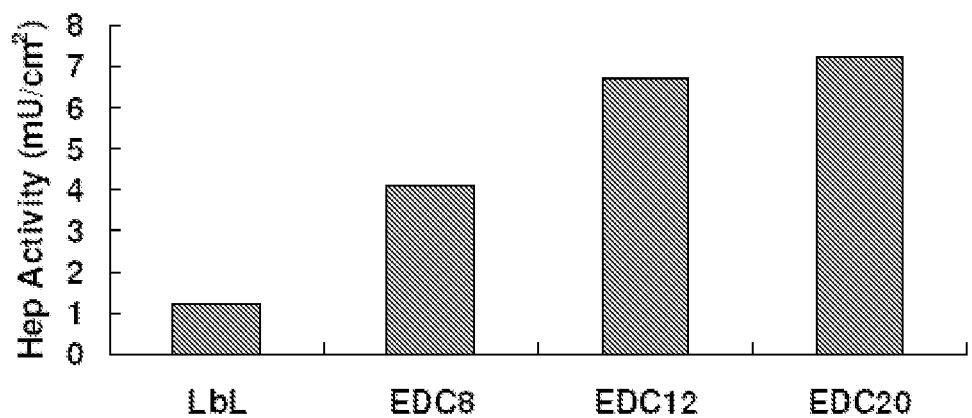
FIG. 22 depicts the comparison of surface heparin activity using an anti-FXa assay with immobilized and solution based heparin.

The anti-coagulant activity of surface immobilized heparin can be measured using anti-factor Xa assay. Results using this assay with LbL immobilized heparin, depicted in FIG. 22, reveal that less covalent attached heparin is need to prevent clotting as compared to various concentrations of heparin in EDC. The surface heparin can be tailored via modulating reaction time, the longer the reaction, the higher the surface anti-coagulation power. In FIG. 22, 1 U=quantity that prevents 1.0 mL of citrated sheep plasma from clotting for 1 h after the addition of 0.2 mL of 10 g/L CaCl$_2$.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Contemplated equivalents of the organoselenium compounds, coatings and compositions described above include such materials which otherwise correspond thereto, and which have the same general properties thereof (e.g., biocompatible, nitric oxide generating), wherein one or more simple variations of substituents are made which do not adversely affect the efficacy of such molecule to achieve its intended purpose. In general, the biocompatible coatings of the present disclosure may be prepared by the methods described herein, or by modifications thereof, using readily available starting materials, reagents and conventional synthesis procedures. In these reactions, it is also possible to make use of variants which are in themselves known, but are not mentioned here.

The present disclosure provides among other things, coatings, compositions, devices, and methods. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Hereby incorporated by reference in their entirety are U.S. Pat. No. 7,128,904, U.S. Pat. No. 7,335,383, and WO/2007/064895.

What is claimed is:

1. A biocompatible coating for a substrate, the biocompatible coating comprising multiple polyanionic/polycationic bilayers comprising at least one organoselenium moiety, wherein each of the polyanionic/polycationic bilayers comprises:
   a layer of a polycationic polymeric material having the at least one organoselenium moiety covalently bonded thereto; and
   a layer of polyanionic material capable of non-covalently bonding to the polycationic polymeric material.

2. The biocompatible coating of claim 1, wherein the polycationic polymeric material comprises at least one of: polyethyleneimine, chitosan, or quaternized polyamide.

3. The biocompatible coating of claim 1, wherein the polyanionic material comprises at least one of: sodium alginate, cellulose sulfate, polyglutamic acid, heparin, or hyaluronic acid.

4. The biocompatible coating of claim 1, wherein the polycationic polymeric material comprises polyethyleneimine.

5. The biocompatible coating of claim 1, wherein the polyanionic material comprises sodium alginate.

6. The biocompatible coating of claim 1, wherein the substrate comprises at least one of a polymer or a biomedically acceptable metal.

7. The biocompatible coating of claim 1, wherein the substrate comprises polyurethane or silicone.

8. The biocompatible coating of claim 1, wherein the organoselenium moiety is selected from the group consisting of selenocystamine, selenocystine, 3,3'-diselenodipropionic acid, selenocysteine, ebselen, propyl-selenocystine, allyl-selenocystine, methyl-selenocystine, selenomethionine, selenium choline, and a diselenium compound.

9. The biocompatible coating of claim 1, wherein the organoselenium moiety is 3,3'-diselenodipropionic acid.

10. The biocompatible coating of claim 1, wherein the biocompatible coating comprises at least four polyanionic/polycationic bilayers.

11. The biocompatible coating of claim 1, wherein the biocompatible coating comprises at least ten polyanionic/polycationic bilayers.

12. The biocompatible coating of claim 1, comprising about 1 μg/cm$^2$ to about 4 μg/cm$^2$Se when the coating is placed on the substrate.

13. The biocompatible coating of claim 1, wherein a maximum NO flux ranges from about 1 mol/(cm$^2$)(min) to about 10 mol/(cm$^2$)(min) when the coating at least partially coats the substrate and the substrate is placed in contact with blood.

14. A medical device comprising the biocompatible coating of claim 1.

15. The medical device of claim 14, wherein the medical device is selected from the group consisting of an intravascular or extravascular medical device, a balloon, a catheter tip, a prosthetic heart valve, a suture, a surgical staple, a synthetic vessel graft, a stent, a stent graft, a vascular or non-vascular graft, a shunt, an aneurysm filler, an intraluminal paving system, a guide wire, an embolic agent, a filter, a drug pump, an arteriovenous shunt, an artificial heart valve, an artificial implant, a foreign body introduced surgically into the blood vessels or at a vascular or non-vascular site, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor, an implantable chemical sensor, an interventional cardiology device, a catheter, and plastic tubing.

16. A method of forming a polymeric coating on a substrate capable of generating nitric oxide in-vivo, comprising:
   a) providing a substrate;
   b) immersing the substrate into a first solution comprising a polycationic polymer covalently bonded to an organoselenium moiety;
   c) immersing the substrate into a second solution comprising a polyanionic polymer; and
   d) repeating b) and c).

17. The method of claim 16, further comprising immersing the substrate in an annealing solution comprising:
   glutathione or S-nitrosoglutathione; and
   phosphate buffered saline.

18. The method of claim 17, wherein the substrate is immersed in the annealing solution for at least one day.

* * * * *